United States Patent
Tobler et al.

(10) Patent No.: US 8,183,416 B2
(45) Date of Patent: May 22, 2012

(54) HETEROCYCLIC AMIDE DERIVATIVES USEFUL AS MICROBIOCIDES

(75) Inventors: Hans Tobler, Basel (CH); Harald Walter, Bsael (CH); Josef Ehrenfreund, Basel (CH); Camilla Corsi, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 82 days.

(21) Appl. No.: 12/765,929

(22) Filed: Apr. 23, 2010

(65) Prior Publication Data

US 2010/0204482 A1 Aug. 12, 2010

Related U.S. Application Data

(62) Division of application No. 12/091,189, filed as application No. PCT/EP2006/010185 on Oct. 23, 2006, now Pat. No. 7,732,469.

(30) Foreign Application Priority Data

Oct. 25, 2005 (EP) .................................. 05023222
Mar. 2, 2006 (EP) .................................. 06004191

(51) Int. Cl.
*C07C 205/06* (2006.01)
(52) U.S. Cl. ........................................ 568/306; 568/929
(58) Field of Classification Search ........................ None
See application file for complete search history.

(56) References Cited

FOREIGN PATENT DOCUMENTS

| JP | 42009824 A1 * | 5/1967 |
| WO | 2004035589 | 4/2004 |
| WO | 2006037632 | 4/2006 |

OTHER PUBLICATIONS

Hiroshi Tanida, Abstract of JP42009824 from STN search report (1967).*
Terabe et al., J. Amer. Chem. Soc., (1973), 95(15), p. 4976-86.*

* cited by examiner

*Primary Examiner* — Yong Chu
(74) *Attorney, Agent, or Firm* — Kody Jones

(57) ABSTRACT

The invention relates to a fungicidally active compound of formula (I):

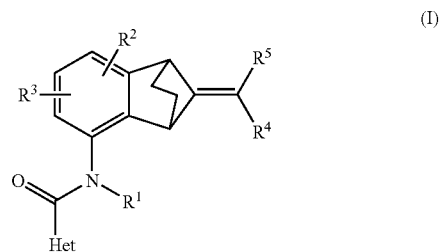

where Het is a 5- or 6-membered heterocyclic ring containing one to three heteroatoms, each independently selected from oxygen, nitrogen and sulphur, the ring being substituted by the groups $R^6$, $R^7$ and $R^8$; $R^1$ is hydrogen, $C_{1-4}$ alkyl, $C_{1-4}$ haloalkyl, $C_{1-4}$alkoxy, $C_{1-4}$haloalkoxy, $CH_2C\!\!=\!\!CR^9$, $CH_2CR^{10}\!\!=\!\!CHR^{11}$, $CH\!\!=\!\!C\!\!=\!\!CH_2$ or $COR^{12}$; $R^2$ and $R^3$ are each, independently, hydrogen, halo, $C_{1-4}$ alkyl, $C_{1-4}$ alkoxy, $C_{1-4}$ haloalkyl or $C_{1-4}$ haloalkoxy; $R^4$ and $R^5$ are each independently selected from halo, cyano and nitro; or one of $R^4$ and $R^5$ is hydrogen and the other is selected from halo, cyano and nitro; $R^6$, $R^7$ and $R^8$ are each, independently, hydrogen, halo, cyano, nitro, $C_{1-4}$ alkyl, $C_{1-4}$ haloalkyl, $C_{1-4}$ alkoxy $(C_{1-4})$alkyl, $C_{1-4}$haloalkoxy$(C_{1-4})$alkyl or $C_{1-4}$haloalkoxy, provided that at least one of $R^6$, $R^7$ and $R^8$ is not hydrogen; $R^9$, $R^{10}$ and $R^{11}$ are each, independently, hydrogen, halo, $C_{1-4}$ alkyl, $C_{1-4}$ haloalkyl or $C_{1-4}$ alkoxy$(C_{1-4})$alkyl; and $R^{12}$ is hydrogen, $C_{1-6}$ alkyl, $C_{1-6}$haloalkyl, $C_{1-4}$ alkoxy$(C_{1-4})$alkyl, $C_{1-4}$ alkylthio$(C_{1-4})$-alkyl, $C_{1-4}$ alkoxy or aryl; to the preparation of these compounds, to novel intermediates used in the preparation of these compounds, to agrochemical compositions which comprise at least one of the novel compounds as active ingredient, to the preparation of the compositions mentioned and to the use of the active ingredients or compositions in agriculture or horticulture for controlling or preventing infestation of plants by phytopathogenic microorganisms, preferably fungi.

9 Claims, No Drawings

HETEROCYCLIC AMIDE DERIVATIVES USEFUL AS MICROBIOCIDES

This application is a divisional application of U.S. Ser. No. 12/091,189 filed Apr. 23, 2008, which is a 371 of International Application No. PCT/EP2006/010185 filed Oct. 23, 2006, which claims priority to EP 005023222.2 filed Oct. 25, 2005 and EP 06004191.0 filed Mar. 2, 2006, the contents of which are incorporated herein by reference.

The present invention relates to novel tricyclic amine derivatives which have microbiocidal activity, in particular fungicidal activity. The invention also relates to the preparation of these compounds, to novel intermediates used in their preparation, to agrochemical compositions which comprise at least one of the novel compounds as active ingredient, to the preparation of the agrochemical compositions and to the use of the active ingredients or compositions in agriculture or horticulture for controlling or preventing infestation of plants by phytopathogenic microorganisms, especially fungi.

The preparation and microbiocidal use of certain tricyclic amine derivatives are described in WO 2004/035589. The present invention is concerned with the provision of alternative tricyclic amine derivatives having microbiocidal activity.

The present invention provides a compound of formula (I):

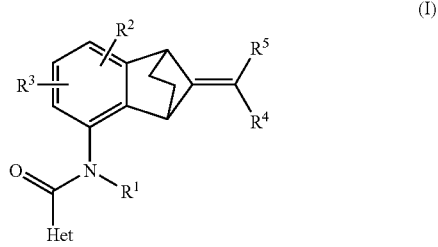

where Het is a 5- or 6-membered heterocyclic ring containing one to three heteroatoms, each independently selected from oxygen, nitrogen and sulphur, the ring being substituted by the groups $R^6$, $R^7$ and $R^8$;

$R^1$ is hydrogen, $C_{1-4}$ alkyl, $C_{1-4}$ haloalkyl, $C_{1-4}$ alkoxy, $C_{1-4}$ haloalkoxy, $CH_2C\!\!=\!\!CR^9$, $CH_2CR^{10}\!\!=\!\!CHR^{11}$, $CH\!\!=\!\!C\!\!=\!\!CH_2$ or $COR^{12}$;

$R^2$ and $R^3$ are each, independently, hydrogen, halo, $C_{1-4}$ alkyl, $C_{1-4}$ alkoxy, $C_{1-4}$ haloalkyl or $C_{1-4}$ haloalkoxy;

$R^4$ and $R^5$ are each independently selected from halo, cyano and nitro; or one of $R^4$ and $R^5$ is hydrogen and the other is selected from halo, cyano and nitro;

$R^6$, $R^7$ and $R^8$ are each, independently, hydrogen, halo, cyano, nitro, $C_{1-4}$ alkyl, $C_{1-4}$ haloalkyl, $C_{1-4}$ alkoxy($C_{1-4}$)alkyl, $C_{1-4}$ haloalkoxy($C_{1-4}$)alkyl or $C_{1-4}$ haloalkoxy, provided that at least one of $R^6$, $R^7$ and $R^8$ is not hydrogen;

$R^9$, $R^{10}$ and $R^{11}$ are each, independently, hydrogen, halo, $C_{1-4}$ alkyl, $C_{1-4}$ haloalkyl or $C_{1-4}$ alkoxy($C_{1-4}$)alkyl; and $R^{12}$ is hydrogen, $C_{1-6}$ alkyl, $C_{1-6}$ haloalkyl, $C_{1-4}$ alkoxy($C_{1-4}$) alkyl, $C_{1-4}$ alkylthio($C_{1-4}$)-alkyl, $C_{1-4}$ alkoxy or aryl.

Halo, either as a lone substituent or in combination with another substituent (e.g. haloalkyl) is generally fluoro, chloro, bromo or iodo, and usually fluoro, chloro or bromo.

Each alkyl moiety (or alkyl moiety of alkoxy, alkylthio, etc.) is a straight or branched chain and, depending on whether it contains 1 to 4 or 1 to 6 carbon atoms, is, for example, methyl, ethyl, n-propyl, n-butyl, n-pentyl, n-hexyl, iso-propyl, sec-butyl, iso-butyl, tent-butyl, neo-pentyl, n-heptyl or 1,3-dimethylbutyl, and usually methyl or ethyl.

Haloalkyl moieties are alkyl moieties which are substituted by one or more of the same or different halogen atoms and are, for example, monofluoromethyl, difluoromethyl, trifluoromethyl, monochloromethyl, dichloromethyl, trichloromethyl, 2,2,2-trifluoroethyl, 2,2-difluoroethyl, 2-fluoroethyl, 1,1-difluoroethyl, 1-fluoroethyl, 2-chloroethyl, pentafluoroethyl, 1,1-difluoro-2,2,2-trichloroethyl, 2,2,3,3-tetrafluoroethyl and 2,2,2-trichloroethyl, and typically trichloromethyl, difluorochloromethyl, difluoromethyl, trifluoromethyl and dichlorofluoromethyl.

Alkoxy is, for example, methoxy, ethoxy, propoxy, iso-propoxy, n-butoxy, iso-butoxy, sec-butoxy and tert-butoxy, and usually methoxy or ethoxy.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy, and usually difluoromethoxy, 2-chloroethoxy and trifluoromethoxy.

Alkylthio is, for example, methylthio, ethylthio, propylthio, iso-propylthio, n-butylthio, iso-butylthio, sec-butylthio or tert-butylthio, and usually methylthio or ethylthio.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Aryl includes phenyl, naphthyl, anthracyl, fluorenyl and indanyl, but is usually phenyl.

The compounds of formula (I) may exist as different geometric or optical isomers or in different tautomeric forms. These may be separated and isolated by well-known (usually chromatographic) techniques, and all such isomers and tautomers and mixtures thereof in all proportions as well as isotopic forms, such as deuterated compounds, are part of the present invention.

In one aspect of the present invention, Het, $R^2$, $R^3$, $R^4$ and $R^5$ are as defined above and $R^1$ is hydrogen, $CH_2C\!\!=\!\!CR^9$, $CH\!\!=\!\!C\!\!=\!\!CH_2$ or $COR^{12}$, wherein $R^9$ and $R^{12}$ are as defined above. Usually $R^1$ is hydrogen, $CH_2C\!\!=\!\!CH$, $CH\!\!=\!\!C\!\!=\!\!CH_2$, $CO(CH_3)$ or $CO(OCH_3)$, typically hydrogen, $CH_2C\!\!=\!\!CH$ or $CH\!\!=\!\!C\!\!=\!\!CH_2$, and preferably hydrogen.

In another aspect of the invention, Het, $R^1$, $R^4$ and $R^5$ are as defined above and $R^2$ and $R^3$ are each, independently, hydrogen, halo (especially fluoro, chloro or bromo), $C_{1-4}$ alkyl (especially methyl) or $C_{1-4}$ alkoxy (especially methoxy). Usually one of $R^2$ and $R^3$ is hydrogen and the other is fluoro, chloro, bromo or methyl (for example, 7-fluoro, 7-chloro, 6-bromo or 7-methyl) or $R^2$ and $R^3$ are both hydrogen, both fluoro, chloro or bromo (for example, 6,8-dibromo) or both methoxy (for example, 6,8-dimethoxy or 7,8-dimethoxy). Typically both $R^2$ and $R^3$ are hydrogen.

In yet another aspect of the invention, Het, $R^1$, $R^2$ and $R^3$ are as defined above and $R^4$ and $R^5$ are both fluoro, chloro, bromo, iodo or cyano or one of $R^4$ and $R^5$ is hydrogen and the other is fluoro, chloro, bromo, iodo, cyano or nitro. Typically $R^4$ and $R^5$ are both fluoro, chloro, bromo, iodo or cyano, and preferably both are fluoro.

It will be appreciated that when $R^4$ and $R^5$ are different, the compound of general formula (I) may exist in the form of (E)- and (Z)-isomers. These may possess different biological properties and may be separated and isolated from mixtures thereof by known chromatographic means. While the present invention includes both isomers separately or in admixture, it has been found satisfactory for microbiocidal use, and particularly for fungicidal use, to employ racemic mixtures.

In still yet another aspect of the invention, $R^1$, $R^2$, $R^3$, $R^4$ and $R^5$ are as defined above and Het is pyrrolyl, pyrazolyl, thiazolyl, oxazolyl, imidazolyl, triazolyl, pyridyl, pyrimidinyl, pyridazinyl, 2,3-dihydro-[1,4]oxathiinyl, oxazinyl, thiazinyl or triazinyl, the rings being substituted by at least one of the groups $R^6$, $R^7$ and $R^8$ as defined above. Usually Het is pyrrolyl (especially pyrrol-3-yl), pyrazolyl (especially pyrazol-4-yl), thiazolyl (especially thiazol-5-yl), oxazolyl (especially oxazol-5-yl), 1,2,3 triazolyl (especially 2-pyridinyl (especially pyrid-3-yl) or 2,3-dihydro-[1,4]oxathiinyl (especially 2,3-dihydro-[1,4]oxathiin-5-yl), typically pyrrol-3-yl, pyrazol-4-yl, thiazol-5-yl or pyrid-3-yl and preferably pyrazol-4-yl.

The substituents of Het ($R^6$, $R^7$ and $R^8$), which are independent of each other, are usually hydrogen, fluoro, chloro, bromo, $C_{1-4}$ alkyl (especially methyl and ethyl), $C_{1-4}$ haloalkyl (especially trifluoromethyl, difluoromethyl, monofluoromethyl and chloro-difluoromethyl) and $C_{1-4}$) alkoxy($C_{1-4}$)alkyl (especially methoxymethyl).

Typical values of Het are the pyrrol-3-yl of the general formula ($Het^1$) and the pyrazol-4-yl of the general formula ($Het^2$):

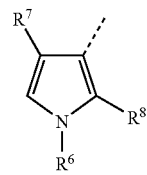

(Het$^1$)

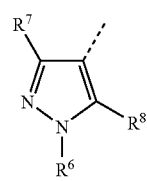

(Het$^2$)

wherein $R^6$ is $C_{1-4}$ alkyl or $C_{1-4}$ alkoxy($C_{1-4}$)alkyl (especially methyl, ethyl or methoxymethyl), $R^7$ is $C_{1-4}$ alkyl or $C_{1-4}$ haloalkyl (especially methyl, trifluoromethyl, difluoromethyl, monofluoromethyl or chlorodifluoromethyl) and $R^8$ is hydrogen or halo (especially hydrogen, fluoro or chloro); the thiazol-5-yl and oxazol-5-yl of the general formula ($Het^3$):

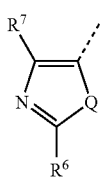

(Het$^3$)

wherein Q is oxygen or sulphur, $R^6$ is $C_{1-4}$ alkyl (especially methyl) and $R^7$ is $C_{1-4}$ alkyl or $C_{1-4}$ haloalkyl (especially methyl or trifluoromethyl); the 1,2,3-triazol-4-yl of the general formula ($Het^4$):

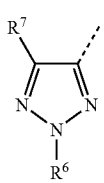

(Het$^4$)

wherein $R^6$ is $C_{1-4}$ alkyl (especially methyl) and $R^7$ is $C_{1-4}$ haloalkyl (especially trifluoromethyl, difluoromethyl or monofluoromethyl); the pyrid-3-yl of the general formula (Het$^5$):

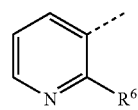

(Het$^5$)

wherein $R^6$ is halo or $C_{1-4}$ haloalkyl (especially chloro, bromo or trifluoromethyl); or the 2,3-dihydro[1,4]oxathiin-5-yl of the general formula (Het$^6$):

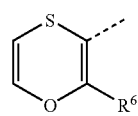

(Het$^6$)

wherein $R^6$ is $C_{1-4}$ alkyl or $C_{1-4}$ haloalkyl (especially methyl or trifluoromethyl).

Compounds of particular interest are those where Het has one of the typical values described immediately above and $R^1$, $R^2$, $R^3$, $R^4$ and $R^5$ have one of the following four sets of values:

1) $R^1$ is hydrogen, $CH_2C\equiv CR^9$, $CH=C=CH_2$ or $COR^{12}$, wherein $R^9$ is hydrogen, halo, $C_{1-4}$ alkyl, $C_{1-4}$ haloalkyl or $C_{1-4}$ alkoxy($C_{1-4}$alkyl and $R^{12}$ is hydrogen, $C_{1-6}$ alkyl, $C_{1-6}$ haloalkyl, $C_{1-4}$ alkoxy($C_{1-4}$)alkyl, $C_{1-4}$ alkylthio($C_{1-4}$alkyl, $C_{1-4}$ alkoxy or aryl; $R^2$ and $R^3$ are each, independently, hydrogen, halo, $C_{1-4}$ alkyl or $C_{1-4}$ alkoxy; and $R^4$ and $R^5$ are both fluoro, chloro, bromo, iodo or cyano or one of $R^4$ and $R^5$ is hydrogen and the other is fluoro, chloro, bromo, iodo, cyano or nitro.

2) $R^1$ is hydrogen, $CH_2C\equiv CH$, $CH=C=CH_2$, $CO(CH_3)$ or $CO(OCH_3)$; one of $R^2$ and $R^3$ is hydrogen and the other is fluoro, chloro, bromo or methyl or $R^2$ and $R^3$ are both hydrogen, both fluoro, both chloro, both bromo or both methoxy; and $R^4$ and $R^5$ are both fluoro, chloro, bromo, iodo or cyano or one of $R^4$ and $R^5$ is hydrogen and the other is fluoro, chloro, bromo, iodo, cyano or nitro.

3) $R^1$ is hydrogen, $CH_2C\equiv CH$ or $CH=C=CH_2$; $R^2$ and $R^3$ are both hydrogen and $R^4$ and $R^5$ are both fluoro, both chloro, both bromo, both iodo or both cyano.

4) $R^1$ is hydrogen; $R^2$ and $R^3$ are both hydrogen; $R^4$ and $R^5$ are both fluoro, both chloro, both bromo, both iodo or both cyano or one of $R^4$ and $R^5$ is hydrogen and the other is fluoro, chloro, bromo, iodo, cyano or nitro.

5) $R^1$ is hydrogen; $R^2$ and $R^3$ are both hydrogen; $R^4$ and $R^5$ are both fluoro, both chloro, both bromo, both iodo or both cyano, preferably both fluoro.

In another aspect of the present invention there is provided a compound of the general formula (I) wherein Het is pyrrol-3-yl substituted at the 1-position by $C_{1-4}$ alkyl or $C_{1-4}$ alkoxy ($C_{1-4}$)alkyl (especially methyl, ethyl or methoxymethyl), substituted at the 4-position by $C_{1-4}$ alkyl or $C_{1-4}$ haloalkyl (especially methyl, difluoromethyl, monofluoromethyl or chloro-difluoromethyl) and optionally substituted at the 2-position by halo (especially fluoro or chloro), pyrazolyl-4-yl substituted at the 1-position by $C_{1-4}$ alkyl or $C_{1-4}$ alkoxy ($C_{1-4}$)alkyl (especially methyl, ethyl or methoxymethyl), substituted at 3-position by $C_{1-4}$ alkyl or $C_{1-4}$ haloalkyl (especially methyl, difluoromethyl, monofluoromethyl or chloro-difluoromethyl) and optionally substituted at the 5-position by halo (especially fluoro or chloro), thiazol-5-yl or oxazol-5-yl substituted at the 2-position by $C_{1-4}$ alkyl (especially methyl) and substituted at the 4-position by $C_{1-4}$ alkyl or $C_{1-4}$ haloalkyl (especially methyl or trifluoromethyl), 2,3-dihydro[1,4]oxathiin-5-yl substituted at the 6-position by $C_{1-4}$ alkyl or $C_{1-4}$ haloalkyl (especially methyl or trifluoromethyl), pyrid-3-yl substituted at the 2-position by halo or $C_{1-4}$ haloalkyl (especially chloro, bromo or trifluoromethyl) or 1,2,3-triazol-4-yl substituted in the 2-position by $C_{1-4}$ alkyl (especially methyl) and in the 5-position by $C_{1-4}$ haloalkyl (especially trifluoromethyl, difluoromethyl and monofluoromethyl); $R^1$ is hydrogen, $CH_2C\equiv CH$, $CH=C=CH_2$ or $COR^{12}$ wherein $R^{12}$ is $C_{1-4}$ alkyl or $C_{1-4}$ alkoxy (especially methyl or methoxy); $R^2$ is hydrogen, 6-halo, 7-halo or 7-$C_{1-4}$ alkyl (especially 6-bromo, 7-chloro, 7-fluoro or 7-methyl), $R^3$ is hydrogen or $R^2$ and $R^3$ together are 6,8-di-$C_{1-4}$ alkoxy, 6,8-dihalo or 7,8-di-$C_{1-4}$ alkoxy (especially 6,8-dimethoxy, 6,8-dibromo or 7,8-dimethoxy); and $R^4$ and $R^5$ are both halo or both cyano or one of $R^4$ and $R^5$ is hydrogen and the other is halo, cyano or nitro (especially both fluoro, chloro, bromo or iodo).

In yet another aspect of the present invention there is provided a compound of the general formula (I) wherein Het is 2-$C_{1-4}$ alkyl-4-$C_{1-4}$haloalkylthiazol-5-yl, 2-halopyrid-3-yl, 1-$C_{1-4}$ alkyl-4-$C_{1-4}$ haloalkylpyrrol-3-yl, 1-$C_{1-4}$ alkyl-3-$C_{1-4}$ haloalkylpyrazol-4-yl or 1-$C_{1-4}$ alkyl-3-$C_{1-4}$ haloalkylpyrazol-4-yl; $R^1$, $R^2$ and $R^3$ are all hydrogen; and $R^4$ and $R^5$ are both halo.

In still yet another aspect of the present invention there is provided a compound of the general formula (I) wherein Het is 2-methyl-4-trifluoromethylthiazol-5-yl, 2-chloro-pyrid-3-yl, 1-methyl-4-trifluoromethylpyrrol-3-yl, 1-methyl-3-trifluoromethylpyrazol-4-yl or 1-methyl-3-difluoromethylpyrazol-4-yl; $R^1$, $R^2$ and $R^3$ are all hydrogen; and $R^4$ and $R^5$ are both fluoro, both chloro or both bromo.

The invention is further illustrated by the individual compounds of formula (I) listed below in Tables 1 to 30. Characterising data is given in Table 31.

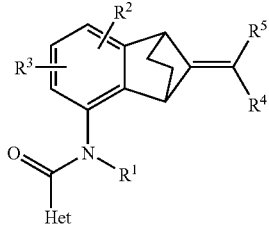

(I)

Tables 1 to 30

Tables 1 to 30 each comprise 69 compounds of the formula (I) in which $R^1$, $R^2$, $R^3$, $R^4$ and $R^5$ have the values given in Table X below and Het has the value given in the relevant Tables 1 to 30 which follow. Thus Table 1 corresponds to Table X when X is 1 and Het has the value given under the Table 1 heading, Table 2 corresponds to Table X when X is 2 and Het has the value given under the Table 2 heading, and so on for Tables 3 to 30.

| Compound No. | $R^1$ | $R^2$, $R^3$ | $R^4$, $R^5$ |
|---|---|---|---|
| X.01 | H | H, H | Cl, Cl |
| X.02 | $CH_2-C\equiv CH$ | H, H | Cl, Cl |
| X.03 | $CH=C=CH_2$ | H, H | Cl, Cl |
| X.04 | $CO(CH_3)$ | H, H | Cl, Cl |
| X.05 | $CO(OCH_3)$ | H, H | Cl, Cl |
| X.06 | H | H, H | H, Cl (E/Z-mixture) |
| X.07 | $CH_2-C\equiv CH$ | H, H | H, Cl (E/Z-mixture) |
| X.08 | $CH=C=CH_2$ | H, H | H, Cl (E/Z-mixture) |
| X.09 | $CO(CH_3)$ | H, H | H, Cl (E/Z-mixture) |
| X.10 | $CO(OCH_3)$ | H, H | H, Cl (E/Z-mixture) |
| X.11 | H | H, H | F, F |
| X.12 | $CH_2-C\equiv CH$ | H, H | F, F |
| X13 | $CH=C=CH_2$ | H, H | F, F |
| X.14 | $CO(CH_3)$ | H, H | F, F |
| X.15 | $CO(OCH_3)$ | H, H | F, F |
| X16 | H | H, H | H, F (E/Z-mixture) |
| X.17 | $CH_2-C\equiv CH$ | H, H | H, F (E/Z-mixture) |
| X.18 | $CH=C=CH_2$ | H, H | H, F (E/Z-mixture) |
| X.19 | $CO(CH_3)$ | H, H | H, F (E/Z-mixture) |
| X.20 | $CO(OCH_3)$ | H, H | H, F (E/Z-mixture) |
| X.21 | H | H, H | Br, Br |
| X.22 | $CH_2-C\equiv CH$ | H, H | Br, Br |
| X23 | $CH=C=CH_2$ | H, H | Br, Br |
| X.24 | $CO(CH_3)$ | H, H | Br, Br |
| X.25 | $CO(OCH_3)$ | H, H | Br, Br |
| X.26 | H | H, H | H, Br (E/Z-mixture) |
| X.27 | $CH_2-C\equiv CH$ | H, H | H, Br (E/Z-mixture) |
| X.28 | $CH=C=CH_2$ | H, H | H, Br (E/Z-mixture) |
| X.29 | $CO(CH_3)$ | H, H | H, Br (E/Z-mixture) |
| X.30 | $CO(OCH_3)$ | H, H | H, Br (E/Z-mixture) |
| X.31 | H | H, H | I, I |
| X.32 | $CH_2-C\equiv CH$ | H, H | I, I |
| X33 | $CH=C=CH_2$ | H, H | I, I |
| X.34 | $CO(CH_3)$ | H, H | I, I |
| X.35 | $CO(OCH_3)$ | H, H | I, I |
| X.36 | H | H, H | H, I (E/Z-mixture) |
| X.37 | $CH_2-C\equiv CH$ | H, H | H, I (E/Z-mixture) |
| X.38 | $CH=C=CH_2$ | H, H | H, I (E/Z-mixture) |
| X.39 | $CO(CH_3)$ | H, H | H, I (E/Z-mixture) |
| X.40 | $CO(OCH_3)$ | H, H | H, I (E/Z-mixture) |
| X.41 | H | H, H | CN, CN |
| X.42 | $CH_2-C\equiv CH$ | H, H | CN, CN |
| X.43 | $CH=C=CH_2$ | H, H | CN, CN |
| X.44 | $CO(CH_3)$ | H, H | CN, CN |
| X.45 | $CO(OCH_3)$ | H, H | CN, CN |
| X.46 | H | H, H | H, CN (E/Z-mixture) |
| X.47 | $CH_2-C\equiv CH$ | H, H | H, CN (E/Z-mixture) |
| X.48 | $CH=C=CH_2$ | H, H | H, CN (E/Z-mixture) |
| X.49 | $CO(CH_3)$ | H, H | H, CN (E/Z-mixture) |
| X.50 | $CO(OCH_3)$ | H, H | H, CN (E/Z-mixture) |
| X.51 | H | H, H | H, $NO_2$ (E/Z-mixture) |
| X.52 | $CH_2-C\equiv CH$ | H, H | H, $NO_2$ (E/Z-mixture) |
| X.53 | $CH=C=CH_2$ | H, H | H, $NO_2$ (E/Z-mixture) |
| X.54 | $CO(CH_3)$ | H, H | H, $NO_2$ (E/Z-mixture) |
| X.55 | $CO(OCH_3)$ | H, H | H, $NO_2$ (E/Z-mixture) |
| X.56 | H | 7-Cl, H | F, F |
| X.57 | H | 7-$CH_3$, H | F, F |
| X.58 | H | 7-F, H | F, F |
| X.59 | H | 6-Br, H | F, F |
| X.60 | H | 6-$OCH_3$, 8-$OCH_3$ | F, F |
| X.61 | H | 7-$OCH_3$, 8-$OCH_3$ | F, F |
| X.62 | H | 6-Br, 8-Br | F, F |
| X.63 | H | 7-Cl, H | H, CN (E/Z-mixture) |
| X.64 | H | 7-$CH_3$, H | H, CN (E/Z-mixture) |
| X.65 | H | 7-F, H | H, CN (E/Z-mixture) |
| X.66 | H | 6-Br, H | H, CN (E/Z-mixture) |
| X.67 | H | 6-$OCH_3$, 8-$OCH_3$ | H, CN (E/Z-mixture) |
| X.68 | H | 7-$OCH_3$, 8-$OCH_3$ | H, CN (E/Z-mixture) |
| X.69 | H | 6-Br, 8-Br | H, CN (E/Z-mixture) |

Table 1 provides 69 compounds of formula (I) where Het is

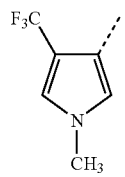

and R$^1$, R$^2$, R$^3$, R$^4$ and R$^5$ are as defined in Table X.

Table 2 provides 69 compounds of formula (I) where Het is

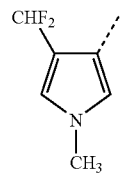

and R$^1$, R$^2$, R$^3$, R$^4$ and R$^5$ are as defined in Table X.

Table 3 provides 69 compounds of formula (I) where Het is

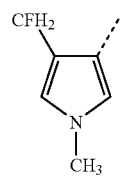

and R$^1$, R$^2$, R$^3$, R$^4$ and R$^5$ are as defined in Table X.

Table 4 provides 69 compounds of formula (I) where Het is

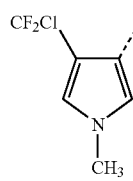

and R$^1$, R$^2$, R$^3$, R$^4$ and R$^5$ are as defined in Table X.

Table 5 provides 69 compounds of formula (I) where Het is

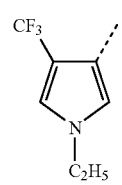

and R$^1$, R$^2$, R$^3$, R$^4$ and R$^5$ are as defined in Table X.

Table 6 provides 69 compounds of formula (I) where Het is

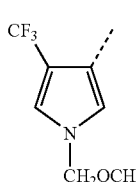

and R$^1$, R$^2$, R$^3$, R$^4$ and R$^5$ are as defined in Table X.

Table 7 provides 69 compounds of formula (I) where Het is

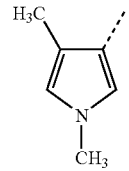

and R$^1$, R$^2$, R$^3$, R$^4$ and R$^5$ are as defined in Table X.

Table 8 provides 69 compounds of formula (I) where Het is

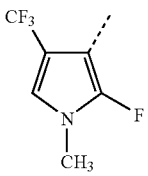

and R$^1$, R$^2$, R$^3$, R$^4$ and R$^5$ are as defined in Table X.

Table 9 provides 69 compounds of formula (I) where Het is

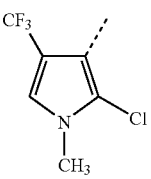

and R$^1$, R$^2$, R$^3$, R$^4$ and R$^5$ are as defined in Table X.

Table 10 provides 69 compounds of formula (I) where Het is

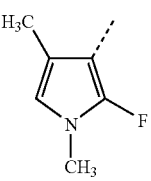

and R$^1$, R$^2$, R$^3$, R$^4$ and R$^5$ are as defined in Table X.

Table 11 provides 69 compounds of formula (I) where Het is

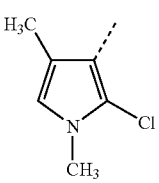

and R$^2$, R$^1$, R$^2$, R$^3$, R$^4$ and R$^5$ are as defined in Table X.

Table 12 provides 69 compounds of formula (I) where Het is

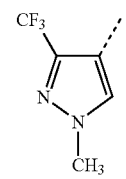

and R$^1$, R$^2$, R$^3$, R$^4$ and R$^5$ are as defined in Table X.

Table 13 provides 69 compounds of formula (I) where Het is

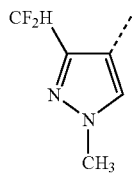

and $R^1$, $R^2$, $R^3$, $R^4$ and $R^5$ are as defined in Table X.

Table 14 provides 69 compounds of formula (I) where Het is

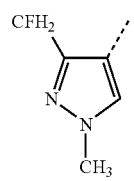

and $R^1$, $R^2$, $R^3$, $R^4$ and $R^5$ are as defined in Table X.

Table 15 provides 69 compounds of formula (I) where Het is

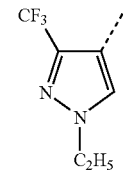

and $R^1$, $R^2$, $R^3$, $R^4$ and $R^5$ are as defined in Table X.

Table 16 provides 69 compounds of formula (I) where Het is

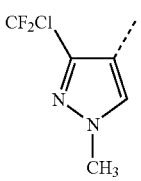

and $R^1$, $R^2$, $R^3$, $R^4$ and $R^5$ are as defined in Table X.

Table 17 provides 69 compounds of formula (I) where Het is

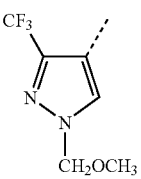

and $R^1$, $R^2$, $R^3$, $R^4$ and $R^5$ are as defined in Table X.

Table 18 provides 69 compounds of formula (I) where Het is

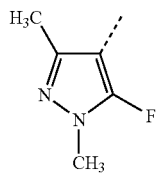

and $R^2$ and $R^1$, $R^2$, $R^3$, $R^4$ and $R^5$ are as defined in Table X.

Table 19 provides 69 compounds of formula (I) where Het is

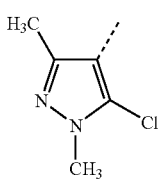

and $R^2$, $R^1$, $R^2$, $R^3$, $R^4$ and $R^5$ are as defined in Table X.

Table 20 provides 69 compounds of formula (I) where Het is

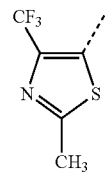

and $R^1$, $R^2$, $R^3$, $R^4$ and $R^5$ are as defined in Table X.

Table 21 provides 69 compounds of formula (I) where Het is

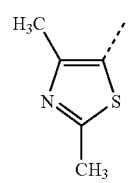

and $R^1$, $R^2$, $R^3$, $R^4$ and $R^5$ are as defined in Table X.

Table 22 provides 69 compounds of formula (I) where Het is

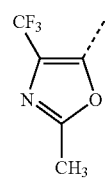

and $R^1$, $R^2$, $R^3$, $R^4$ and $R^5$ are as defined in Table X.

Table 23 provides 69 compounds of formula (I) where Het is

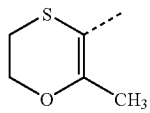

and R¹, R², R³, R⁴ and R⁵ are as defined in Table X.

Table 24 provides 69 compounds of formula (I) where Het is

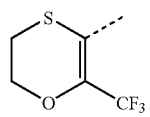

and R², R¹, R², R³, R⁴ and R⁵ are as defined in Table X.

Table 25 provides 69 compounds of formula (I) where Het is

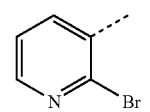

and R¹, R², R³, R⁴ and R⁵ are as defined in Table X.

Table 26 provides 69 compounds of formula (I) where Het is

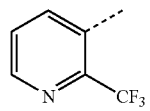

and R¹, R², R³, R⁴ and R⁵ are as defined in Table X.

Table 27 provides 69 compounds of formula (I) where Het is

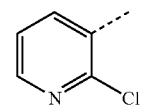

and R¹, R², R³, R⁴ and R⁵ are as defined in Table X.

Table 28 provides 69 compounds of formula (I) where Het is

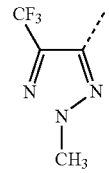

and R¹, R², R³, R⁴ and R⁵ are as defined in Table X.

Table 29 provides 69 compounds of formula (I) where Het is

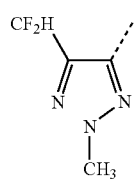

and R¹, R², R³, R⁴ and R⁵ are as defined in Table X.

Table 30 provides 69 compounds of formula (I) where Het is

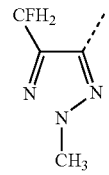

and R¹, R², R³, R⁴ and R⁵ are as defined in Table X.

Table 31

Table 31 shows selected melting point and selected NMR data, all with $CDCl_3$ as the solvent, unless otherwise stated, for compounds of Tables 1 to 30. No attempt is made to list all characterising data in all cases.

In Table 31 and throughout the description that follows, temperatures are given in degrees Celsius; "NMR" means nuclear magnetic resonance spectrum; MS stands for mass spectrum; "%" is percent by weight, unless corresponding concentrations are indicated in other units; and the following abbreviations are used:

m.p.=melting point b.p.=boiling point.
s=singlet br=broad
d=doublet dd=doublet of doublets
t=triplet q=quartet
m=multiplet ppm=parts per million
THF=tetrahydrofuran

TABLE 31

| Compund No. | m.p (° C.) | ¹H-NMR proton shifts δ (ppm) ($CDCl_3$) |
|---|---|---|
| 1.01 | 183-188 | 7.78 (d, 1H), 7.70 (brd, exchangeable with $D_2O$, 1H), 7.39 (brd s, 1H), 7.16 (t, 1H), 7.01 (d overlapped from brd s, 2H), 4.00 (m, 1H), 3.94 (m, 1H), 3.72 (s, 3H), 2.10 (m, 2H), 1.51 (m, 1H), 1.38 (m, 1H). |
| 1.11 | 133-135 | 7.76 (d, 1H), 7.70 (brd, exchangeable with $D_2O$, 1H), 7.39 (brd s, 1H), 7.13 (t, 1H), 7.01 (brd s, 1H), 7.00 (d, 1H), 3.98 (m, 1H), 3.93 (m, 1H), 3.72 (s, 3H), 2.04 (m, 2H), 1.49 (m, 1H), 1.36 (m, 1H). |

TABLE 31-continued

| Compund No. | m.p (° C.) | $^1$H-NMR proton shifts δ (ppm) (CDCl$_3$) |
|---|---|---|
| 1.21 | 155-158 | 7.79 (d, 1H), 7.70 (brd, exchangeable with D$_2$O, 1H), 7.39 (brd s, 1H), 7.17 (t, 1H), 7.02 (d, 1H), 7.01 (brd s, 1H), 3.98 (m, 1H), 3.91 (m, 1H), 3.72 (s, 3H), 2.11 (m, 2H), 1.50 (m, 1H), 1.39 (m, 1H). |
| 12.01 | 179-181 | 8.06 (s, 1H), 7.69 (d overlapped by brd signal, exchangeable with D$_2$O, 2H), 7.18 (t, 1H), 7.06 (d, 1H), 4.00 (s, 3H), 3.96 (m, 2H), 2.12 (m, 2H), 1.51 (m, 1H), 1.39 (m, 1H). |
| 12.11 | 137-143 | 8.06 (s, 1H), 7.68 (brd, exchangeable with D$_2$O, 1H), 7.67 (d, 1H), 7.14 (d, 1H), 4.00 (s, 3H), 3.94 (m, 2H), 2.06 (m, 2H), 1.48 (m, 1H), 1.36 (m. 1H). |
| 12.21 | 198-200 | 8.06 (s, 1H), 7.71 (d, 1H), 7.68 (brd, exchangeable with D$_2$O, 1H), 7.18 (t, 1H), 7.05 (d, 1H), 4.00 (s, 3H), 3.95 (m, 1H), 3.93 (m, 1H), 2.12 (m, 2H), 1.50 (m, 1H), 1.38 (m, 1H). |
| 13.01 | 148-150 | 8.11 (brd, exchangeable with D$_2$O, 1H), 8.06 (s, 1H), 7.82 (d, 1H), 7.17 (t, 1H), 7.03 (d, 1H), 6.89 (t, $J_{HF}$ = 54 Hz, 1H), 4.06 (m, 1H), 3.95 (s, 3H, overlapped by m, 1H), 2.10 (m, 2H), 1.49 (m, 1H), 1.38 (m, 1H). |
| 13.11 | 144-147 | 8.10 (brd, exchangeable with D$_2$O, 1H), 8.06 (s, 1H), 7.78 (d, 1H), 7.14 (t, 1H), 7.01 (d, 1H), 6.89 (t, $J_{HF}$ = 54 Hz, 1H), 4.03 m, 1H), 3.96 (s, 3H), 3.93 (m, 1H), 2.04 (m, 2H), 1.47 (m, 1H), 1.36 (m, 1H). |
| 13.21 | 143-145 | 8.10 (brd, exchangeable with D$_2$O, 1H), 8.06 (s, 1H), 7.83 (d, 1H), 7.18 (t, 1H), 7.03 (d, 1H), 6.88 (t, $J_{HF}$ = 54 Hz, 1H), 4.03 (m, 1H), 3.96 (s, 3H), 3.92 (m, 1H), 2.11 (m, 2H), 1.48 (m, 1H), 1.37 (m, 1H). |
| 20.01 | 136-139 | 7.74 (brd, exchangeable with D$_2$O, 1H), 7.60 (d, 1H), 7.19 (t, 1H), 7.10 (d, 1H), 3.97 (m, 2H), 2.78 (s, 3H), 2.12 (m, 2H), 1.52 (m, 1H), 1.39 (m, 1H). |
| 20.11 | 125-127 | 7.74 (brd, exchangeable with D$_2$O, 1H), 7.58 (d, 1H), 7.16 (t, 1H), 7.08 (d, 1H), 3.95 (m, 2H), 2.78 (s, 3H), 2.06 (m, 2H), 1.49 (m, 1H), 1.37 (m, 1H). |
| 20.21 | 155-157 | 7.73 (brd, exchangeable with D$_2$O, 1H), 7.61 (d, 1H), 7.20 (t, 1H), 7.10 (d, 1H), 3.94 (m, 2H), 2.78 (s, 3H), 2.14 (m, 2H), 1.51 (m, 1H), 1.38 (m, 1H). |
| 27.01 | 175-177 | 8.54 (d, 1H), 8.26 (d, 1H), 8.16 (brd, exchangeable with D$_2$O, 1H), 7.66 (d, 1H), 7.44 (dd, 1H), 7.21 (dd, 1H), 7.10 (d, 1H), 4.06 (m, 1H), 3.98 (m, 1H), 2.13 (m, 2H), 1.57 (m, 1H), 1.42 (m, 1H). |
| 27.11 | 109-115 | 8.54 (d, 1H), 8.28 (d, 1H), 8.16 (brd, exchangeable with D$_2$O, 1H), 7.64 (d, 1H), 7.44 (dd, 1H), 7.18 (t, 1H), 7.08 (d, 1H), 4.04 (m, 1H), 3.97 (m, 1H), 2.09 (m, 2H), 1.55 (m, 1H), 1.41 (m, 1H). |
| 27.21 | 185-187 | 8.55 (d, 1H), 8.27 (d, 1H), 8.15 (brd, exchangeable with D$_2$O, 1H), 7.67 (d, 1H), 7.44 (dd, 1H), 7.22 (dd, 1H), 7.10 (d, 1H), 4.04 (m, 1H), 3.95(m, 1H), 2.16 (m, 2H), 1.41 (m, 1H), 1.26 (m, 1H). |

The compounds of formula (I) may be prepared as described below with reference to reaction Schemes 1 to 4.

Scheme 1

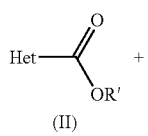

(II)

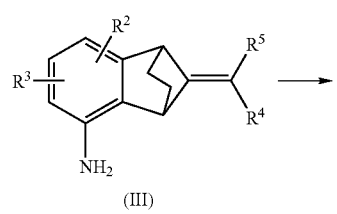

(III)

-continued

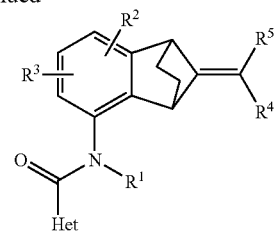

(I)

As shown in Scheme 1, a compound of formula (I), where R$^1$ is hydrogen and Het, R$^2$, R$^3$, R$^4$ and R$^5$ are as defined above, may be synthesized by reacting a compound of formula (II), where Het is as defined above and R' is C$_{1-5}$ alkyl, with an aniline of formula (III), where R$^2$, R$^3$, R$^4$ and R$^5$ are as defined above, in the presence of NaN(TMS)$_2$ at –10° C. to ambient temperature, preferably in dry THF, as described by J. Wang et al. *Synlett*, 2001, 1485.

Scheme 2

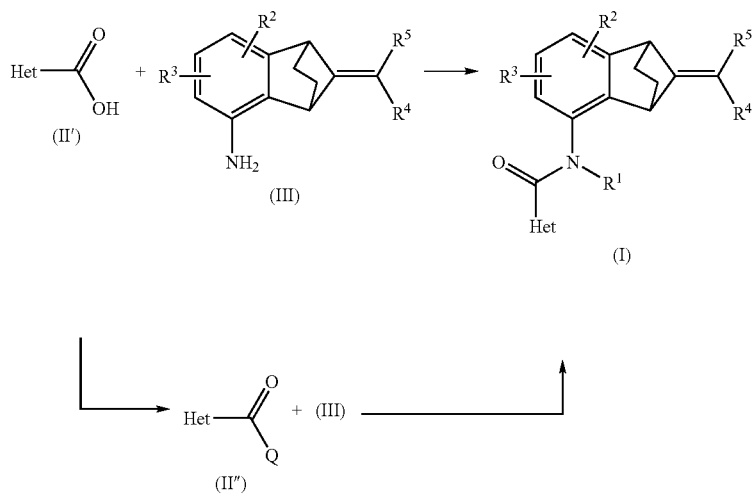

Alternatively, as shown in Scheme 2, a compound of formula (I), where $R^1$ is hydrogen and Het, $R^2$, $R^3$, $R^4$ and $R^5$ are as defined above, may be prepared by reacting a compound of formula (II'), where Het is as defined above, with an aniline of formula (III), where $R^2$, $R^3$, $R^4$ and $R^5$ are as defined above, in the presence of an activating agent, such as BOP-Cl (bis-(2-oxo-3-oxazolidinyl)-phosphinic acid), and two equivalents of a base, such as triethylamine, in a solvent, such as dichloromethane (as described, for example, by J. Cabré et al, Synthesis 1984, 413) or by reacting a compound of formula (II"), where Het is as defined above and Q is chloro, fluoro or bromo, with an aniline of formula (III), where $R^2$, $R^3$, $R^4$ and $R^5$ are as defined above, in the presence of one equivalent of a base, such as triethylamine or sodium or potassium carbonate or bicarbonate, in a solvent, such as dichloromethane, ethyl acetate or N,N-dimethylformamide, preferably at −10 to 30° C. The compound of formula (II") is obtained from a compound of formula (II') by treatment with a halogenating agent such as thionyl chloride, thionyl bromide, oxalyl chloride, phosgene, $SF_4$/HF, DAST ((diethylamino)sulphur trifluoride), or Deoxo-Fluor® ([bis(2-methoxyethyl)amino]-sulphur trifluoride) in a solvent such as toluene, dichloromethane or acetonitrile.

Scheme 3

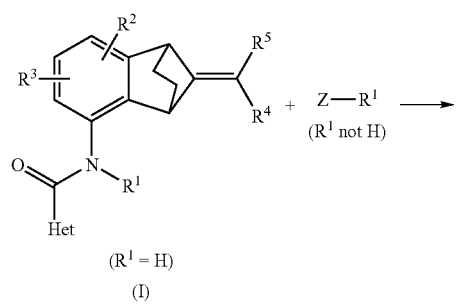

-continued

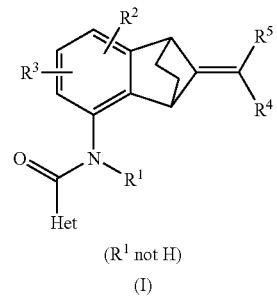

A compound of formula (I), where $R^1$ is other than hydrogen and Het, $R^2$, $R^3$, $R^4$ and $R^5$ are as defined above, may be prepared by reacting a compound of formula (I), where $R^1$ is hydrogen and Het, $R^2$, $R^3$, $R^4$ and $R^5$ are as defined above, with a species $Z$—$R^1$, where $R^1$ is as defined above but is not hydrogen and Z is preferably chloro, bromo or iodo or Z is such that $Z$—$R^1$ is an anhydride (that is, when $R^1$ is $COR^{12}$, Z is $OCOR^{12}$) in the presence of a base, for example sodium hydride, tsodium or potassium hydroxide, $NaN(TMS)_2$, triethylamine, sodium bicarbonate or potassium carbonate, in an appropriate solvent, such as ethyl acetate, or in a biphasic mixture, such as a dichloromethane/water mixture, at −10 to 30° C.

The compounds (II) and (II') are generally known compounds and may be prepared as described in the chemical literature or obtained from commercial sources. The compound (III) is a novel compound and may be prepared as described with reference to Scheme 4.

Scheme 4

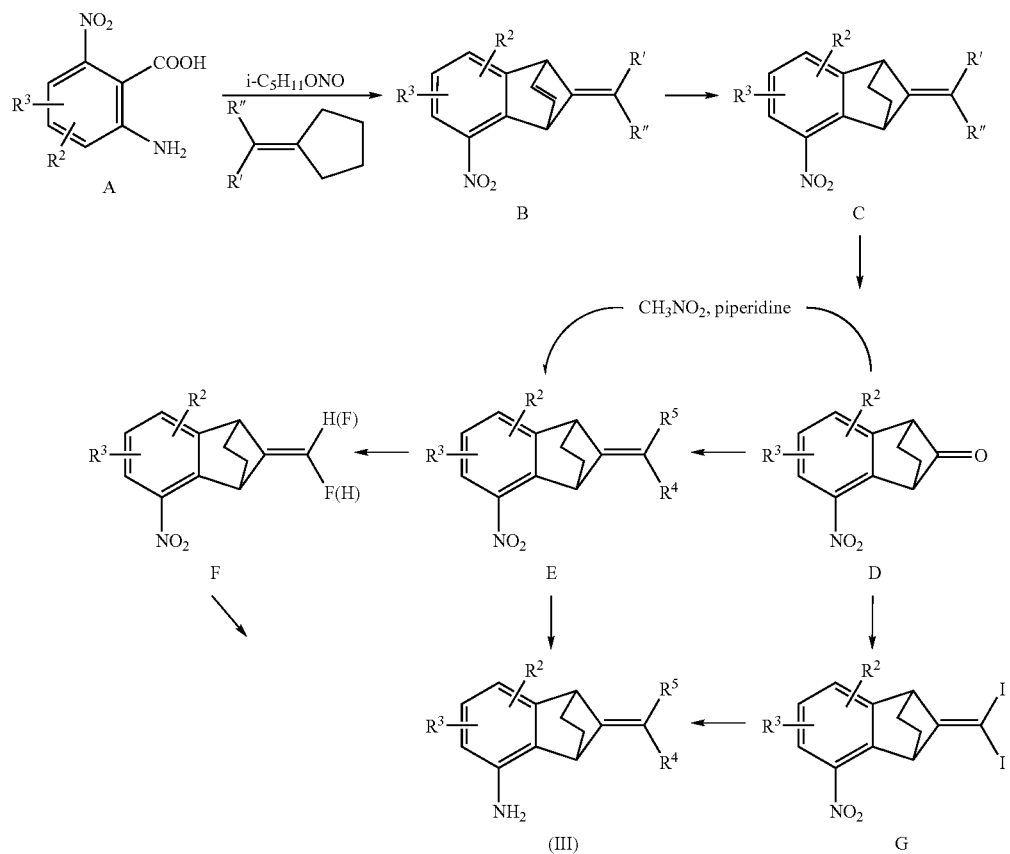

As shown in Scheme 4, the compound of formula (III) may be prepared by a Bechamp reduction or by other established methods, for example, by selective catalytic hydrogenation, of the nitro-compounds (E), (F) and (G).

The 9-dihalomethylidene-5-nitro-benzonorbornenes (E), where $R^4$ and $R^5$ are chloro, bromo or fluoro, may be obtained by the Wittig olefination of the ketones (D) with in situ generated dihalomethylidene phosphoranes $R'''_3P=C(R^4)R^5$, where $R'''$ is triphenyl, tri $C_{1-4}$ alkyl or tridimethylamine and $R^4$ and $R^5$ are halo, according to or by analogy with the procedures described by H-D. Martin et al, *Chem. Ber.* 118, 2514 (1985), S. Hayashi et al, *Chem. Lett.* 1979, 983, or M. Suda, *Tetrahedron Letters,* 22, 1421 (1981).

E/Z-mixtures of the 9-monohalomethylidene-5-nitro-benzonorbornenes (E), where $R^4$ is hydrogen and $R^5$ is chloro, bromo or iodo, may be prepared from the compound (D) by analogy with the procedure described in *Tetrahedron Letters,* 37, 1913 (1996), *Synthesis,* 1087 (2003) or *Tetrahedron Letters* 43, 2725 (2002). Mixed dihalomethylidenes may be obtained by methods described by P. Knochel, *Synthesis,* 1797 (2003).

The 9-cyano-methylidene-5-nitro-benzonorbornenes (E), where $R^4$ is hydrogen and $R^5$ is cyano, may be prepared by the Wittig olefination of the ketones (D) with cyano-methylidene phosphoranes or from 9-dicyano-methylidene derivatives by basic condensation with malodinitrile, both according to established methods in the literature. E/Z-mixtures of 9-Nitro-methylidene-5-nitro-benzonorbornene (E), where $R^4$ is hydrogen and $R^5$ is nitro, may be obtained through the basic condensation of ketone (D) with nitromethane in the presence of piperidine under the conditions described by Y. Jang et al, *Tetrahedron* 59, 4979 (2003).

E/Z-mixtures of 9-monofluoromethylidene-5-nitro-benzonorbornenes (F) may be obtained by the treatment of 9-difluoromethylidene-5-nitro-benzonorbornenes (E), where $R^4$ and $R^5$ are both fluoro, with reducing agents such as Red-Al®, LiAlH$_4$, AlH(Bu-i) or n-Bu-Li as described by S. Hayashi et al, *Chem. Lett.* 1979, 983, X. Huang et al, *J. Org. Chem.* 65, 627 (2000), Y. Li et al, *Organic Letters* 6, 4467 (2004) and A. Oky et at *J. Org. Chem.* 53, 3089 (1988). Preferred solvents are tetrahydrofuran, ether and toluene.

The 9-diiodomethylidenes (G), where $R^4$ and $R^5$ are both iodo, may be obtained from compounds (D) by a method developed by Duhamel using LiHMDS (2 equivalents), ICH$_2$P(O)(OEt)$_2$ and iodine in tetrahydrofuran at $-78°$ C. for two hours (*Synthesis,* 1071 (1993) and *J. Org. Chem.* 64, 8770 (1999)).

The 9-oxo-5-nitro-benzonorbornenes (D) may be obtained using standard ozonolysis conditions (in dichloromethane at $-70°$ C.) from 9-alkylidene-benzonorbornenes (C) followed by a reductive work up involving reducing agents such as triphenylphosphine (J. J. Pappas et al, *J. Org. Chem.* 33, 787 (1968), dimethyl sulphide (J. J. Pappas et al, *Tetrahedron Letters,* 7, 4273 (1966), trimethyl phosphite (W. S. Knowles et al, *J. Org. Chem.* 25, 1031 (1960), or zinc/acetic acid (R. Muneyuki and H. Tanida, *J. Org. Chem.* 31, 1988 (1966). Commonly used solvents are, for example, dichloromethane, chloroform and methanol.

The 5-nitro-benzonorbornenes (C), where R' is hydrogen or $C_{1-4}$ alkyl and R" is $C_{1-4}$ alkyl or $C_{3-6}$ cycloalkyl or R' and R" together with the carbon atom to which they are attached form a 4-6 membered cycloalkyl ring and $R^2$ and $R^3$ are as defined above, may be prepared by the selective hydrogenation of the compounds (B) using Pd/C (or other suitable catalysts such as Ra/Ni) with the absorption of 1 equivalent of hydrogen under ice cooling by analogy with the procedures of R. Muneyuki and H. Tanida, J. Org. Chem. 31, 1988 (1966). Other conditions are hydrogenation under homogeneous catalysis (e.g. Wilkinson catalyst, chlorotris(triphenylphoshine)rhodium, or equivalents, in tetrahydrofuran, toluene, dichloromethane, ethyl acetate, methanol, etc. at ambient temperature.

The 9-alkylidene-5-nitro-benzonorbornadienes (B), where R' is hydrogen or $C_{1-4}$ alkyl and R" is $C_{1-4}$ alkyl or $C_{3-6}$ cycloalkyl or R' and R" together with the carbon atom to which they are attached form a 4-6 membered cycloalkyl ring and $R^2$ and $R^3$ are as defined above, may be prepared by the addition of an in situ generated benzyne [for example, starting from a 6-nitroanthranilic acid of formula (A), as described by L. Paquette et al, J. Amer. Chem. Soc. 99, 3734 (1977) or from other suitable precursors (see H. Pellissier et al. Tetrahedron, 59, 701 (2003), R. Muneyuki and H. Tanida, J. Org. Chem. 31, 1988 (1966)] to a 6-alkyl- or 6,6-dialkylfulvene according to or by analogy with one of the procedures described by R. Muneyuki and H. Tanida, J. Org. Chem. 31, 1988 (1966), P. Knochel et al, Angew. Chem. 116, 4464 (2004), J. W. Coe et al, Organic Letters 6, 1589 (2004), L. Paquette et al, J. Amer. Chem. Soc. 99, 3734 (1977), R. N. Warrener et al, Molecules, 6, 353 (2001), R. N. Warrener et al, Molecules, 6, 194 (2001). Suitable aprotic solvents for this process include diethyl ether, butyl methyl ether, ethyl acetate, dichloromethane, acetone, tetrahydrofuran, toluene, 2-butanone and dimethoxyethane. Reaction temperatures range from room temperature to 100° C., preferably 35-80° C.

6-Alkyl- or 6,6-dialkylfulvenes are prepared as described by M. Neuenschwander et al, Helv. Chim. Acta, 54, 1037 (1971), ibid 48, 955 (1965), R. D. Little et al, J. Org. Chem. 49, 1849 (1984), I. Erden et al, J. Org. Chem. 60, 813 (1995) and S. Collins et al, J. Org. Chem. 55, 3395 (1990).

6-Nitroanthranilic acids of formula (A) are generally known compounds and may be prepared as described in the chemical literature or obtained from commercial sources.

The intermediate compounds of the formulae (B), (C), (D), (E), (F), (G) and (III), are novel compounds and form further aspects of the present invention.

In particular, the invention includes a compound of the formula (B):

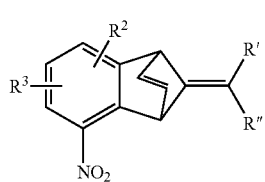

(B)

including the E- and Z-isomers individually, where they exist, or in admixture, where R' is hydrogen or $C_{1-4}$ alkyl and R" is $C_{1-4}$ alkyl, or $C_{3-6}$ cycloalkyl or R' and R", together with the carbon atom to which they are attached, form a 4 to 6 membered cycloalkyl ring and $R^2$ and $R^3$ are are each, independently, hydrogen, halo, $C_{1-4}$ alkyl, $C_{1-4}$ alkoxy, $C_{1-4}$haloalkyl or $C_{1-4}$haloalkoxy.

Suitably, $R^2$ and $R^3$ are each, independently, hydrogen, halo (especially fluoro, chloro or bromo), $C_{1-4}$ alkyl (especially methyl) or $C_{1-4}$ alkoxy (especially methoxy). Usually, one of $R^2$ and $R^3$ is hydrogen and the other is fluoro, chloro, bromo or methyl (for example, 7-fluoro, 7-chloro, 6-bromo or 7-methyl) or $R^2$ and $R^3$ are both hydrogen, both fluoro, chloro or bromo (for example, 6,8-dibromo) or both methoxy (for example, 6,8-dimethoxy or 7,8-dimethoxy).

Of particular interest are compounds of the formula (B) where R' and R" are as defined above, $R^2$ is hydrogen, 6-halo, 7-halo or 7-$C_{1-4}$ alkyl (especially 6-bromo, 7-chloro, 7-fluoro or 7-methyl), and $R^3$ is hydrogen or $R^2$ and $R^3$ together are 6,8-di-$C_{1-4}$ alkoxy, 6,8-dihalo or 7,8-di-$C_{1-4}$ alkoxy (especially 6,8-dimethoxy, 6,8-dibromo or 7,8-dimethoxy). Of especial interest are compounds of the formula (B) where R' and R" are as defined above, $R^2$ is hydrogen, 6-halo, 7-halo or 7-$C_{1-4}$ alkyl (especially 6-bromo, 7-chloro, 7-fluoro or 7-methyl), and $R^3$ is hydrogen or $R^2$ and $R^3$ together are 6,8-di-$C_{1-4}$ alkoxy, 6,8-dihalo or 7,8-di-$C_{1-4}$ alkoxy (especially 6,8-dimethoxy, 6,8-dibromo or 7,8-dimethoxy). Typically, both $R^2$ and $R^3$ are hydrogen.

Illustrative of the compounds of formula (B) are the compounds listed in Table 32 below. Characterising data for these compounds are given in Table 33.

TABLE 32

| Compound No. | R' | R" | $R^2$ | $R^3$ |
| --- | --- | --- | --- | --- |
| 32.01 | $C_2H_5$ | $C_2H_5$ | H | H |
| 32.02 | $CH_3$ | $CH_3$ | H | H |
| 32.03* | H | $CH_3$ | H | H |
| 32.04* | H | $C_2H_5$ | H | H |
| 32.05* | H | iso-$C_3H_7$ | H | H |
| 32.06* | H | cyclopropyl | H | H |
| 32.07* | H | cyclohexyl | H | H |
| 32.08 | —$C_3H_6$— | | H | H |
| 32.09 | —$C_4H_8$— | | H | H |
| 32.10 | —$C_5H_{10}$— | | H | H |
| 32.11 | n-$C_3H_7$ | n-$C_3H_7$ | H | H |
| 32.12* | H | n-$C_3H_7$ | H | H |
| 32.13* | $CH_3$ | $C_2H_5$ | H | H |
| 32.14 | $CH_3$ | $CH_3$ | 7-Cl | H |
| 32.15 | $CH_3$ | $CH_3$ | 7-$CH_3$ | H |
| 32.16 | $CH_3$ | $CH_3$ | 7-F | H |
| 32.17 | $CH_3$ | $CH_3$ | 6-Br | H |
| 32.18 | $CH_3$ | $CH_3$ | 6-$OCH_3$ | 8-$OCH_3$ |
| 32.19 | $CH_3$ | $CH_3$ | 7-$OCH_3$ | 8-$OCH_3$ |
| 32.20 | $CH_3$ | $CH_3$ | 6-Br | 8-Br |

*indicates E/Z-mixtures

TABLE 33

| Compound No. | Physical Data | NMR, δ (ppm) (CDCl$_3$) |
|---|---|---|
| 32.01 | m.p. 60-61° C. | $^1$H: 7.70 (d, 1H), 7.42 (d, 1H), 7.06 (t, 1H), 6.99 (m, 2H), 5.31 (br s, 1H), 4.46 (br s, 1H), 1.96 (m, 4H), 0.89 (t, 6H). |
| 32.02 | m.p. 95-96° C. | $^1$H: 7.70 (d, 1H), 7.41 (d, 1H), 7.07 (t, 1H), 6.99 (m, 2H), 5.34 (br s, 1H), 4.47 (br s, 1H), 1.57 (2s, 6H). $^{13}$C: 159.83, 154.30, 147.33, 144.12, 142.89, 141.93, 125.23 (2 C's), 119.32, 105.68, 50.51, 50.44, 19.05, 18.90. |
| 32.05 | viscous oil | $^1$H: 7.72 (2xd, 1H), 7.43 (2xd, 1H), 7.08 (2xt, 1H), 6.92 (m, 2H), 5.34 and 4.47 (each br s), 5.02 and 4.18 (each br s): the 4 signals account for 2H, 4.43 (2xd, 1H), 2.41 (m, 1H), 0.96 (m, 3H), 0.83 (m, 3H). |
| 32.06 | viscous oil | $^1$H: 7.73 (2xd, 1H), 7.49 and 7.40 (each d, together 1H), 7.08 (2xt, 1H), 7.02 (m, 2H); 5.46, 5.06, 4.35 and 4.22 (each br s, together 2H); 1.36 (m, 1H), 0.66 (m, 2H), 0.26 and 0.21 (2xm, 2H). |
| 32.09 | m.p. 102-103° C. | $^1$H: 7.71 (d, 1H), 7.41 (d, 1H), 7.06 (t, 1H), 6.99 (m, 2H), 5.17 (br s, 1H), 4.31 (br s, 1H), 2.19 (m, 4H), 1.59 (m, 4H). |

The invention also includes a compound of the formula (C):

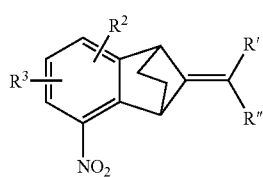

including the E- and Z-isomers individually, where they exist, or in admixture, where R' is hydrogen or $C_{1-4}$ alkyl and R" is $C_{1-4}$ alkyl, or $C_{3-6}$ cycloalkyl or R' and R", together with the carbon atom to which they are attached, form a 4 to 6 membered cycloalkyl ring and $R^2$ and $R^3$ are are each, independently, hydrogen, halo, $C_{1-4}$ alkyl, $C_{1-4}$ alkoxy, $C_{1-4}$ haloalkyl or $C_{1-4}$ haloalkoxy.

Suitably, $R^2$ and $R^3$ are each, independently, hydrogen, halo (especially fluoro, chloro or bromo), $C_{1-4}$ alkyl (especially methyl) or $C_{1-4}$ alkoxy (especially methoxy). Usually, one of $R^2$ and $R^3$ is hydrogen and the other is fluoro, chloro, bromo or methyl (for example, 7-fluoro, 7-chloro, 6-bromo or 7-methyl) or $R^2$ and $R^3$ are both hydrogen, both fluoro, chloro or bromo (for example, 6,8-dibromo) or both methoxy (for example, 6,8-dimethoxy or 7,8-dimethoxy).

Of particular interest are compounds of the formula (C) where R' and R" are as defined above, $R^2$ is hydrogen, 6-halo, 7-halo or 7-$C_{1-4}$ alkyl (especially 6-bromo, 7-chloro, 7-fluoro or 7-methyl), and $R^3$ is hydrogen or $R^2$ and $R^3$ together are 6,8-di-$C_{1-4}$ alkoxy, 6,8-dihalo or 7,8-di-$C_{1-4}$ alkoxy (especially 6,8-dimethoxy, 6,8-dibromo or 7,8-dimethoxy). Of especial interest are compounds of the formula (C) where R' and R" are as defined above, $R^2$ is hydrogen, 6-halo, 7-halo or 7-$C_{1-4}$ alkyl (especially 6-bromo, 7-chloro, 7-fluoro or 7-methyl), and $R^3$ is hydrogen or $R^2$ and $R^3$ together are 6,8-di-$C_{1-4}$ alkoxy, 6,8-dihalo or 7,8-di-$C_{1-4}$ alkoxy (especially 6,8-dimethoxy, 6,8-dibromo or 7,8-dimethoxy). Typically, both $R^2$ and $R^3$ are hydrogen.

Illustrative of the compounds of formula (C) are the compounds listed in Table 34 below. Characterising data for these compounds are given in Table 35.

TABLE 34

| Compound No. | R' | R" | $R^2$ | $R^3$ |
|---|---|---|---|---|
| 34.01 | $C_2H_5$ | $C_2H_5$ | H | H |
| 34.02 | $CH_3$ | $CH_3$ | H | H |
| 34.03* | H | $CH_3$ | H | H |
| 34.04* | H | $C_2H_5$ | H | H |
| 34.05* | H | iso-$C_3H_7$ | H | H |
| 34.06* | H | cyclopropyl | H | H |
| 34.07* | H | cyclohexyl | H | H |
| 34.08 | —$C_3H_6$— | | H | H |
| 34.09 | —$C_4H_8$— | | H | H |
| 34.10 | —$C_5H_{10}$— | | H | H |
| 34.11 | n-$C_3H_7$ | n-$C_3H_7$ | H | H |
| 34.12* | H | n-$C_3H_7$ | H | H |
| 34.13* | $CH_3$ | $C_2H_5$ | H | H |
| 34.14 | $CH_3$ | $CH_3$ | 7-Cl | H |
| 34.15 | $CH_3$ | $CH_3$ | 7-$CH_3$ | H |
| 34.16 | $CH_3$ | $CH_3$ | 7-F | H |
| 34.17 | $CH_3$ | $CH_3$ | 6-Br | H |
| 34.18 | $CH_3$ | $CH_3$ | 6-$OCH_3$ | 8-$OCH_3$ |
| 34.19 | $CH_3$ | $CH_3$ | 7-$OCH_3$ | 8-$OCH_3$ |
| 34.20 | $CH_3$ | $CH_3$ | 6-Br | 8-Br |

*indicates E/Z-mixtures

TABLE 35

| Compound No. | Physical Data | NMR, δ (ppm) (CDCl$_3$) |
|---|---|---|
| 34.01 | m.p. 55-56° C. | $^1$H: 7.83 (d, 1H), 7.41 (d, 1H), 7.18 (t, 1H), 4.66 (m, 1H), 3.88 (m, 1H), 2.01 (m, 2 + 4H), 1.31 (m, 2H), 0.93 (t, 6H). |
| 34.02 | m.p. 88-89° C. | $^1$H: 7.83 (d, 1H), 7.42 (d, 1H), 7.19 (t, 1H), 4.68 (m, 1H), 3.87 (m, 1H), 2.00 (m, 2H), 1.64 (s, 6H), 1.34 (m, 1H), 1.24 (m, 1H). |

TABLE 35-continued

| Compound No. | Physical Data | NMR, δ (ppm) (CDCl₃) |
|---|---|---|
| | | $^{13}$C: 150.99, 146.26, 143.16, 142.14, 126.03, 125.18, 120.39, 113.80, 43.68, 43.54, 26.65, 25.67, 19.96, 19.80. |

The invention further includes a compound of the formula (D):

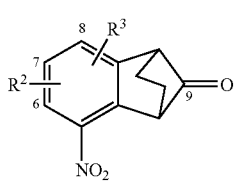

(D)

where $R^2$ and $R^3$ are each, independently, hydrogen, halo, $C_{1-4}$ alkyl, $C_{1-4}$ alkoxy, $C_{1-4}$haloalkyl or $C_{1-4}$haloalkoxy.

Suitably, $R^2$ and $R^3$ are each, independently, hydrogen, halo (especially fluoro, chloro or bromo), $C_{1-4}$ alkyl (especially methyl) or $C_{1-4}$ alkoxy (especially methoxy). Usually, one of $R^2$ and $R^3$ is hydrogen and the other is fluoro, chloro, bromo or methyl (for example, 7-fluoro, 7-chloro, 6-bromo or 7-methyl) or $R^2$ and $R^3$ are both hydrogen, both fluoro, chloro or bromo (for example, 6,8-dibromo) or both methoxy (for example, 6,8-dimethoxy or 7,8-dimethoxy).

Of particular interest are compounds of the formula (D) where $R^2$ is hydrogen, 6-halo, 7-halo or 7-$C_{1-4}$ alkyl (especially 6-bromo, 7-chloro, 7-fluoro or 7-methyl), and $R^3$ is hydrogen or $R^2$ and $R^3$ together are 6,8-di-$C_{1-4}$ alkoxy, 6,8-dihalo or 7,8-di-$C_{1-4}$ alkoxy (especially 6,8-dimethoxy, 6,8-dibromo or 7,8-dimethoxy). Of especial interest are compounds of the formula (D) where $R^2$ is hydrogen, 6-halo, 7-halo or 7-$C_{1-4}$ alkyl (especially 6-bromo, 7-chloro, 7-fluoro or 7-methyl), and $R^3$ is hydrogen or $R^2$ and $R^3$ together are 6,8-di-$C_{1-4}$ alkoxy, 6,8-dihalo or 7,8-di-$C_{1-4}$ alkoxy (especially 6,8-dimethoxy, 6,8-dibromo or 7,8-dimethoxy). Typically, both $R^2$ and $R^3$ are hydrogen.

Illustrative of the compounds of formula (D) are the compounds listed with characterising data in Table 36 below.

The invention further includes a compound of the formula (E):

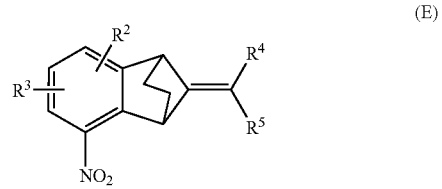

(E)

including the E- and Z-isomers individually, where they exist, or in admixture, where $R^2$ and $R^3$ are are each, independently, hydrogen, halo, $C_{1-4}$ alkyl, $C_{1-4}$ alkoxy, $C_{1-4}$haloalkyl or $C_{1-4}$haloalkoxy; and $R^4$ and $R^5$ are each, independently, halo, cyano or nitro, or one of $R^4$ and $R^5$ is hydrogen.

Suitably, $R^2$ and $R^3$ are each, independently, hydrogen, halo (especially fluoro, chloro or bromo), $C_{1-4}$ alkyl (especially methyl) or $C_{1-4}$ alkoxy (especially methoxy). Usually, one of $R^2$ and $R^3$ is hydrogen and the other is fluoro, chloro, bromo or methyl (for example, 7-fluoro, 7-chloro, 6-bromo or 7-methyl) or $R^2$ and $R^3$ are both hydrogen, both fluoro, chloro or bromo (for example, 6,8-dibromo) or both methoxy (for example, 6,8-dimethoxy or 7,8-dimethoxy).

Of particular interest are compounds of the formula (E) where $R^2$ is hydrogen, 6-halo, 7-halo or 7-$C_{1-4}$ alkyl (especially 6-bromo, 7-chloro, 7-fluoro or 7-methyl), and $R^3$ is hydrogen or $R^2$ and $R^3$ together are 6,8-di-$C_{1-4}$ alkoxy, 6,8-dihalo or 7,8-di-$C_{1-4}$ alkoxy (especially 6,8-dimethoxy, 6,8-dibromo or 7,8-dimethoxy). Of especial interest are compounds of the formula (E) where $R^2$ is hydrogen, 6-halo, 7-halo or 7-$C_{1-4}$ alkyl (especially 6-bromo, 7-chloro, 7-fluoro or 7-methyl), and $R^3$ is hydrogen or $R^2$ and $R^3$ together are 6,8-di-$C_{1-4}$ alkoxy, 6,8-dihalo or 7,8-di-$C_{1-4}$ alkoxy (especially 6,8-dimethoxy, 6,8-dibromo or 7,8-dimethoxy). Typically, both $R^2$ and $R^3$ are hydrogen.

TABLE 36

| Cmpd No. | $R^2$ | $R^3$ | Physical data | NMR, δ (ppm) (CDCl₃) |
|---|---|---|---|---|
| 36.01 | H | H | m.p. 112-114° C. | $^1$H: 8.07 (d, 1H), 7.62 (d, 1H), 7.41 (t, 1H), 4.25 (d, 1H), 3.49 (d, 1H), 2.35 (m, 2H), 1.53 (m, 1H), 1.41 (m, 1H). $^{13}$C: 203.79, 143.51, 143.03, 136.10, 127.17 (2x), 122.31, 46.98 (2x), 22.32, 21.35. |
| 36.02 | 7-Cl | H | | |
| 36.03 | 7-CH3 | H | | |
| 36.04 | 7-F | H | | |
| 36.05 | 6-Br | H | | |
| 36.06 | 6-OCH₃ | 8-OCH₃ | | |
| 36.07 | 7-OCH₃ | 8-OCH₃ | | |
| 36.08 | 6-Br | 8-Br | | |

Suitably, $R^4$ and $R^5$ are both fluoro, chloro, bromo, iodo or cyano or one of $R^4$ and $R^5$ is hydrogen and the other is fluoro, chloro, bromo, iodo, cyano or nitro. Typically both $R^4$ and $R^5$ are both fluoro, chloro, bromo, iodo or cyano, and preferably both are fluoro.

A sub-group of the compounds (E) are the compounds (F):

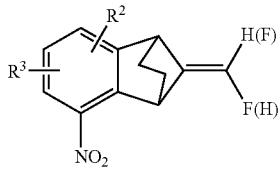
(F)

including the E- and Z-isomers individually or in admixture, where $R^2$ and $R^3$ are each, independently, hydrogen, halo, $C_{1-4}$ alkyl, $C_{1-4}$ alkoxy, $C_{1-4}$ haloalkyl or $C_{1-4}$ haloalkoxy. Particular values of $R^2$ and $R^3$ are as described for compounds (E) above.

Another sub-group of the compounds (E) are the compounds (G):

(G)

where $R^2$ and $R^3$ are each, independently, hydrogen, halo, $C_{1-4}$ alkyl, $C_{1-4}$ alkoxy, $C_{1-4}$ haloalkyl or $C_{1-4}$ haloalkoxy. Particular values of $R^2$ and $R^3$ are as described for compounds (E) above.

Illustrative of the compounds of formula (E), (F) and (G) are the compounds listed in Table 37 below. Characterising data for these compounds are given in Table 38.

TABLE 37

| Compound No. | $R^2$ | $R^3$ | $R^4$ | $R^5$ |
|---|---|---|---|---|
| 37.01 | H | H | F | F |
| 37.02 | H | H | Cl | Cl |
| 37.03 | H | H | Br | Br |
| 37.04 | H | H | I | I |
| 37.05* | H | H | F | H |
| 37.06* | H | H | Cl | H |
| 37.07* | H | H | Br | H |
| 37.08* | H | H | I | H |
| 37.09 | H | H | CN | CN |
| 37.10* | H | H | CN | H |
| 37.11* | H | H | $NO_2$ | H |
| 37.12 | 7-Cl | H | F | F |
| 37.13 | 7-$CH_3$ | H | F | F |
| 37.14 | 7-F | H | F | F |
| 37.15 | 6-Br | H | F | F |
| 37.16 | 6-$OCH_3$ | 8-$OCH_3$ | F | F |
| 37.17 | 7-$OCH_3$ | 8-$OCH_3$ | F | F |
| 37.18 | 6-Br | 8-Br | F | F |

*indicates E/Z-mixtures

TABLE 38

| Compound No. | Physical Data | NMR, δ (ppm) ($CDCl_3$) |
|---|---|---|
| 37.01 | m.p. 99-101° C. | $^1$H: 7.9 (d, 1H), 7.45 (d, 1H), 7.26 (t, 1H), 4.82 (m, 1H), 4.03 (m, 1H), 2.17 (m, 2H), 1.46 (m, 1H), 1.38 (m, 1H). $^{13}$C: 149.27, 145.75 (t, 276.7 Hz), 142.04, 141.27, 127.13, 125.46, 121.18, 103.73 (t, 103.73 (t, 25 Hz), 42.26, 42.17, 27.22, 26.18. |
| 37.02 | m.p. 136-137° C. | $^1$H: 7.94 (d, 1H), 7.48 (d, 1H), 7.30 (t, 1H), 4.82 (m, 1H), 4.05 (m, 1H), 2.22 (m, 2H), 1.48 (m, 1H), 1.37 (m, 1H). $^{13}$C: 150.02, 147.95, 142.22, 140.15, 127.34, 125.91, 121.53, 105.42, 46.54 (2x), 26.33, 25.27. |
| 37.03 | m.p. 153-155° C. | $^1$H: 7.94 (d, 1H), 7.49 (d, 1H), 7.31 (t, 1H), 4.79 (m, 1H), 4.03 (m, 1H), 2.23 (m, 2H), 1.47 (m, 1H), 1.35 (m, 1H); $^{13}$C: 156.88, 147.58, 142.32, 139.83, 127.36, 126.00, 121.61, 72.62, 48.80 (2x), 26.08, 25.00. |

The invention still further includes a compound of the formula (III):

(III)

including the E- and Z-isomers individually, where they exist, or in admixture, where $R^2$ and $R^3$ are each, independently, hydrogen, halo, $C_{1-4}$ alkyl, $C_{1-4}$ alkoxy, $C_{1-4}$ haloalkyl or $C_{1-4}$ haloalkoxy; and $R^4$ and $R^5$ are each, independently, halo, cyano or nitro, or one of $R^4$ and $R^5$ is hydrogen.

Suitably, $R^2$ and $R^3$ are each, independently, hydrogen, halo (especially fluoro, chloro or bromo), $C_{1-4}$ alkyl (especially methyl) or $C_{1-4}$ alkoxy (especially methoxy). Usually, one of $R^2$ and $R^3$ is hydrogen and the other is fluoro, chloro, bromo or methyl (for example, 7-fluoro, 7-chloro, 6-bromo or 7-methyl) or $R^2$ and $R^3$ are both hydrogen, both fluoro, chloro or bromo (for example, 6,8-dibromo) or both methoxy (for example, 6,8-dimethoxy or 7,8-dimethoxy).

Of particular interest are compounds of the formula (III) where $R^2$ is hydrogen, 6-halo, 7-halo or 7-$C_{1-4}$ alkyl (especially 6-bromo, 7-chloro, 7-fluoro or 7-methyl), and $R^3$ is hydrogen or $R^2$ and $R^3$ together are 6,8-di-$C_{1-4}$ alkoxy, 6,8-dihalo or 7,8-di-$C_{1-4}$ alkoxy (especially 6,8-dimethoxy, 6,8-dibromo or 7,8-dimethoxy). Of especial interest are compounds of the formula (III) where $R^2$ is hydrogen, 6-halo, 7-halo or 7-$C_{1-4}$ alkyl (especially 6-bromo, 7-chloro, 7-fluoro or 7-methyl), and $R^3$ is hydrogen or $R^2$ and $R^3$ together are 6,8-di-$C_{1-4}$ alkoxy, 6,8-dihalo or 7,8-di-$C_{1-4}$ alkoxy (especially 6,8-dimethoxy, 6,8-dibromo or 7,8-dimethoxy). Typically, both $R^2$ and $R^3$ are hydrogen.

Suitably, $R^4$ and $R^5$ are both fluoro, chloro, bromo, iodo or cyano or one of $R^4$ and $R^5$ is hydrogen and the other is fluoro, chloro, bromo, iodo, cyano or nitro. Typically both $R^4$ and $R^5$ are both fluoro, chloro, bromo, iodo or cyano, and preferably both are fluoro.

Illustrative of the compounds of formula (III) are the compounds listed in Table 39 below. Characterising data for these compounds are given in Table 40.

TABLE 39

| Compound No. | $R^2$ | $R^3$ | $R^4$ | $R^5$ |
|---|---|---|---|---|
| 39.01 | H | H | F | F |
| 39.02 | H | H | Cl | Cl |
| 39.03 | H | H | Br | Br |
| 39.04 | H | H | I | I |
| 39.05* | H | H | F | H |
| 39.06* | H | H | Cl | H |
| 39.07* | H | H | Br | H |
| 39.08* | H | H | I | H |
| 39.09 | H | H | CN | CN |
| 39.10* | H | H | CN | H |
| 39.11* | H | H | $NO_2$ | H |
| 39.12 | 7-Cl | H | F | F |
| 39.13 | 7-$CH_3$ | H | F | F |
| 39.14 | 7-F | H | F | F |
| 39.15 | 6-Br | H | F | F |
| 39.16 | 6-$OCH_3$ | 8-$OCH_3$ | F | F |
| 39.17 | 7-$OCH_3$ | 8-$OCH_3$ | F | F |
| 39.18 | 6-Br | 8-Br | F | F |

*indicates E/Z-mixtures

TABLE 38

| Compound No. | Physical Data | NMR, δ (ppm) ($CDCl_3$) |
|---|---|---|
| 39.01 | m.p. 99-101° C. | $^1$H: 6.94 (t, 1H), 6.66 (d, 1H), 6.50 (d, 1H), 3.91 (m, 1H), 3.86 (m, 1H), 3.72 (br, 2H, exchangeable with $D_2O$), 2.01 (m, 2H), 1.36 (m, 2H). $^{13}$C: 147.16, 144.93 (t, $J_{C-F}$ = 277 Hz), 138.50, 130.00, 127.18, 113.94, 110.99, 104.49 (t, $J_{C(9)-F}$ = 25 Hz), 42.62, 38.43, 27.59, 26.78. |
| 39.02 | m.p. 136-137° C. | $^1$H: 6.96 (t, 1H), 6.66 (d, 1H), 6.52 (d, 1H), 3.91 (m, 1H), 3.87 (m, 1H), 3.62 (br, 2H, exchangeable with $D_2O$), 2.06 (m, 2H), 1.37 (m, 2H). $^{13}$C: 151.55, 145.97, 138.92, 128.83, 127.49, 114.10, 111.23, 102.71, 47.18, 43.01, 26.70, 25.88. |
| 39.03 | m.p. 153-155° C. | $^1$H: 6.96 (t, 1H), 6.65 (d, 1H), 6.52 (d, 1H), 3.87 (m, 1H), 3.84 (m, 1H), 3.62 (br, 2H, exchangeable with $D_2O$), 2.08 (m, 2H), 1.35 (m, 2H). $^{13}$C: 145.61, 139.00, 128.48, 127.50, 114.12, 111.30, 69.89, 49.50, 45.34, 26.42, 25.62. |

It has now been found that the compounds of formula (I) according to the invention have, for practical purposes, a very advantageous spectrum of activities for protecting useful plants against diseases that are caused by phytopathogenic microorganisams, such as fungi, bacteria or viruses.

The invention relates to a method of controlling or preventing infestation of useful plants by phytopathogenic microorganisms, wherein a compound of formula (I) is applied as acitve ingredient to the plants, to parts thereof or the locus thereof. The compounds of formula (I) according to the invention are distinguished by excellent activity at low rates of application, by being well tolerated by plants and by being environmentally safe. They have very useful curative, preventive and systemic properties and are used for protecting numerous useful plants. The compounds of formula (I) can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula (I) as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds of formula (I) according to the invention may be used for controlling fungi in related areas, for example in the protection of technical materials, including wood and wood related technical products, in food storage or in hygiene management.

The compounds of formula (I) are, for example, effective against the phytopathogenic fungi of the following classes: Fungi imperfecti (e.g. *Botrytis, Pyricularia, Helminthosporium, Fusarium, Septoria, Cercospora* and *Alternaria*) and Basidiomycetes (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Good activity has been observed against Asian soybean rust (*Phakopsora pachyrhizi*). Good activity has also been observed against rust diseases, such as *Puccinia recondita* spp. Furthermore, the novel compounds of formula (I) are effective against phytopathogenic bacteria and viruses (e.g. against *Xanthomonas* spp, *Pseudomonas* spp, *Erwinia amylovora* as well as against the tobacco mosaic virus).

Within the scope of the invention, useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus Bacillus.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula (I) can be used in unmodified form or, preferably, together with carriers and adjuvants conventionally employed in the art of formulation.

Therefore the invention also relates to compositions for controlling and protecting against phytopathogenic microorganisms, comprising a compound of formula (I) and an inert carrier, and to a method of controlling or preventing infestation of useful plants by phytopathogenic microorganisms, wherein a composition, comprising a compound of formula (I) as acitve ingredient and an inert carrier, is applied to the plants, to parts thereof or the locus thereof.

To this end compounds of formula (I) and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula (I) or compositions, comprising a compound of formula (I) as acitve ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula (I), or a composition, comprising a compound of formula (I) as acitve ingredient and an inert carrier, is foliar application. The frequency of application and the rate of application will depend on the risk of infestation by the corresponding pathogen. However, the compounds of formula (I) can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula (I) may also be applied to seeds (coating) by impregnating the seeds or tubers either with a liquid formulation of the fungicide or coating them with a solid formulation.

A formulation, i.e. a composition comprising the compound of formula (I) and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula (I), 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to lkg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the application (location, timing, application method) and can, owing to these parameters, vary within wide limits.

The compounds of formula (I), or a pharmaceutical salt thereof, described above may also an advantageous spectrum of activity for the treatment and/or prevention of microbial infection in an animal.

"Animal" can be any animal, for example, insect, mammal, reptile, fish, amphibian, preferably mammal, most preferably human. "Treatment" means the use on an animal which has microbial infection in order to reduce or slow or stop the increase or spread of the infection, or to reduce the infection or to cure the infection. "Prevention" means the use on an animal which has no apparent signs of microbial infection in order to prevent any future infection, or to reduce or slow the increase or spread of any future infection.

According to the present invention there is provided the use of a compound of formula (I) in the manufacture of a medicament for use in the treatment and/or prevention of microbial infection in an animal. There is also provided the use of a compound of formula (I) as a pharmaceutical agent. There is also provided the use of a compound of formula (I) as an antimicrobial agent in the treatment of an animal. According to the present invention there is also provided a pharmaceutical composition comprising as an active ingredient a compound of formula (I), or a pharmaceutically acceptable salt thereof, and a pharmaceutically acceptable diluent or carrier. This composition can be used for the treatment and/or prevention of antimicrobial infection in an animal. This pharmaceutical composition can be in a form suitable for oral administration, such as tablet, lozenges, hard capsules, aqueous suspensions, oily suspensions, emulsions dispersible powders, dispersible granules, syrups and elixirs. Alternatively this pharmaceutical composition can be in a form suitable for topical application, such as a spray, a cream or lotion. Alternatively this pharmaceutical composition can be in a form suitable for parenteral administration, for example injection. Alternatively this pharmaceutical composition can be in inhalable form, such as an aerosol spray.

The compounds of formula (I) may be effective against various microbial species able to cause a microbial infection in an animal. Examples of such microbial species are those causing Aspergillosis such as *Aspergillus fumigatus, A. flavus, A. terrus, A. nidulans* and *A. niger*; those causing Blastomycosis such as *Blastomyces dermatitidis*; those causing Candidiasis such as *Candida albicans, C. glabrata, C. tropicalis, C. parapsilosis, C. krusei* and *C. lusitaniae*; those causing Coccidioidomycosis such as *Coccidioides immitis*; those causing Cryptococcosis such as *Cryptococcus neoformans*; those causing Histoplasmosis such as *Histoplasma capsulatum* and those causing Zygomycosis such as *Absidia corymbifera, Rhizomucor pusillus* and *Rhizopus arrhizus*. Further examples are *Fusarium* Spp such as *Fusarium oxysporum* and *Fusarium solani* and *Scedosporium* Spp such as *Scedosporium apiospermum* and *Scedosporium prolificans*. Still further examples are *Microsporum* Spp, *Trichophyton* Spp, *Epidermophyton* Spp, *Mucor* Spp, *Sporothorix* Spp, *Phialophora* Spp, *Cladosporium* Spp, *Petriellidium* spp, *Paracoccidioides* Spp and *Histoplasma* Spp.

The following non-limiting Examples illustrate the above-described invention in more detail.

EXAMPLE 1

This Example illustrates the preparation of 2-Methyl-4-trifluoromethyl-thiazole-5-carboxylic acid (9-dichloromethylidene-benzonorbornene-5-yl)amide (Compound No. 20.01)

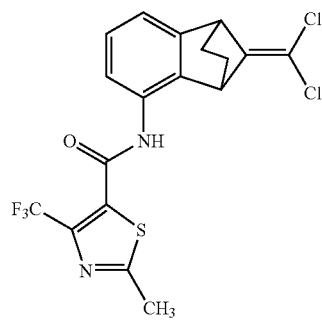

9-Dichloromethylidene-5-amino-benzonorbornene (175 mg, 0.73 mmol), 2-methyl-4-trifluoromethyl-thiazole-5-carboxylic acid (162 mg, 0.77 mmol, 1.05 eq.) and triethylamine (184 mg, 1.8 mmol, 2.5 eq.) were reacted with bis-(2-oxo-3-oxazolidinyl)-phosphinic acid chloride (278 mg, 1.09 mmol, 1.5 eq.) in dichloromethane (10 ml) at 25° C. for 20 hours. The reaction mixture in ethyl acetate was washed successively with water and saturated. Sodium chloride solution, dried over sodium sulphate, evaporated and purified on silica gel (ethyl acetate-hexane-(1:2) to give 250 mg colourless crystals (m.p. 136-139° C.).

EXAMPLE 2

This Example illustrates the preparation of 9-(3-pentylidene)-5-nitro-benzonorbornadiene (Compound No. 32.01):

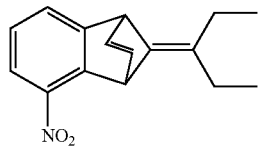

To a well stirred solution of isopentylnitrite (2.31 ml, 1.3 eq.) in dimethoxyethane (50 ml) at 58° C. a mixture of 6-nitroanthranilic acid (2.76 g, 1 eq.) and 6,6-diethylfulvene (6.45 g of 79% purity, 2.5 eq.) dissolved in 25 ml dimethoxyethane was added dropwise within 8 minutes whilst the temperature rose to 67° C. After 30 minutes the dark reaction mixture was evaporated and purified on silica gel in hexane-ethyl acetate-(20:1) to give 3.02 g (78%) of the desired product as an oil that solidified at room temperature (m.p. 60-61° C.).

EXAMPLE 3

This Example illustrates the preparation of 9-(3-pentylidene)-5-nitro-benzonorbornene (Compound No. 34.01):

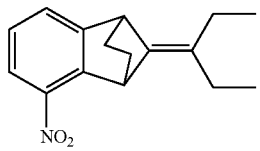

Compound 32.01 (7.97 g prepared as described in Example 2) in THF (70 ml) was hydrogenated at 20° C. in the presence of Rh(PPh$_3$)$_3$Cl (Wilkinson's catalyst; 0.8 g). The reaction ceased after uptake of one equivalent of hydrogen. Evaporation and filtration of the crude on silica gel in ethyl acetate-hexane-(100:2) gave the desired product as an oil (7.90 g) that solidified on standing at room temperature (m.p. 69-56° C.).

EXAMPLE 4

This Example illustrates the preparation of 9-Oxo-5-nitro-benzonorbornene (Compound No. 36.01)

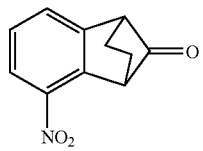

Compound 34.01 (7.0 g, 27.2 mmol; prepared as described in Example 3) dissolved in dichloromethane (300 ml) and methanol (5 ml) was ozonized (2.8 l O$_2$/min, 100 Watt, corresponding to 9.7 g O$_3$/h) at −70° C. until a persistent blue colour was observed (after approximately 15 minutes). The reaction mixture was flushed with nitrogen gas. Triphenylphosphine (8.4 g, 32.03 mmol, 1.18 eq.) was added and the temperature was allowed to warm up to 20-25° C. After evaporation of the solvent the residue was purified on silica gel in hexane-EtOAc-3:1 to give 5.2 g of Compound 36.01 (m.p. 112-114° C.).

EXAMPLE 5

This Example illustrates the preparation of 9-difluoromethylidene-5-nitro-benzonorbornene (Compound No. 37.01)

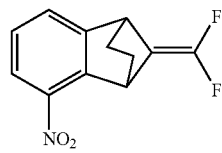

To a solution of dibromodifluoromethane (6.30 g, 30 mmol) at 0° C. in THF (50 ml) was added tris-(dimethylamino)-phosphane (10.1 g at 97%, equivalent to 11.2 ml, 60 mmol) in THF (30 ml) within 20 minutes. To the resulting suspension, after stirring for 1 hour at room temperature, was added dropwise a solution of 9-oxo-5-nitro-benzonorbornene (Compound 36.01) (6.10 g, 30 mmol; prepared as described in Example 4) in THF (20 ml) within 25 minutes followed by stirring for 21 hours. The suspension was poured onto ice-water and extracted with ethyl acetate. Purification on silica gel in ethyl acetate-hexane-(1:4) yielded 4.675 g of Compound 37.01 (m.p. 99-101° C.).

EXAMPLE 6

This Example illustrates the preparation of 2. 9-Dichloromethylidene-5-nitro-benzonorbornene (Compound No. 37.02)

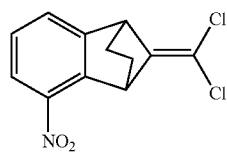

Dry carbon tetrachloride (5.9 g, 33 mmol) was reacted with triphenylphosphine (14.46 g, 55.1 mmol) in dichloromethane (30 ml) at room temperature for 1 hour. 9-Oxo-5-nitro-benzonorbornene (Compound 36.01) (5.60 g, 27.56 mmol; prepared as described in Example 4) in dichloromethane (10 ml) was added dropwise and stirred for 20 hours at room temperature. After aqueous work-up (ice-water) and extraction with dichloromethane, the crude product was purified on silica gel in ethyl acetate-hexane-(1:4) to obtain of the desired compound 37.02 (1.83 g; m.p. 136-137° C.). Some starting material (4.06 g) was recovered.

EXAMPLE 7

This Example illustrates the preparation of 3. 9-Dibromomethylidene-5-nitro-benzonorbornene (Compound No. 37.03)

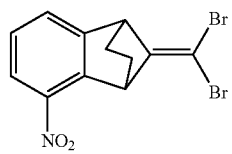

Carbon tetrabromide (4.66 g at 98%, 13.8 mmol) was reacted under stirring with triphenylphosphine (7.23 g, 27.6 mmol) in dichloromethane (50 ml) for 50 minutes at room temperature. 9-Oxo-5-nitro-benzonorbornene (Compound 36.01) (2.8 g, 13.8 mmol; prepared as described in Example 4) in dichloromethane (10 ml) was added dropwise and stirred overnight at room temperature. Aqueous work-up (ice-water) and extraction with dichloromethane followed by column chromatography (ethyl acetate-hexane-(1:9) of the crude product yielded the desired product Compound 37.03 (2.1 g; m.p. 153-155° C.).

EXAMPLE 8

This Example illustrates the preparation of 9-difluoromethylidene-5-amino-benzonorbornene (Compound No. 39.01)

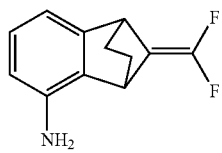

9-Difluoromethylidene-5-nitro-benzonorbornene (Compound 37.01) (3.0 g, 12.65 mmol; prepared as described in Example 5) in a mixture of THF (25 ml) and 5% aqueous acetic acid (8 ml) is reacted with iron powder (a total of 6.29 g) at reflux temperature, added in 3 portions over 4 hours, for 22 hours. The reaction mixture, after filtering over Hyflo® and aqueous work-up in ether, was purified on silica gel in ethyl acetate-hexane-(1:4) to give the desired aniline Compound 39.01 (2.06 g).

EXAMPLE 9

This Example illustrates the preparation of 9-Isopropylidene-5-nitro-benzonorbornadiene (Compound No. 32.02)

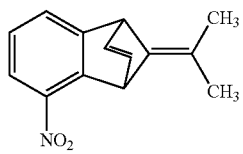

A mixture of 110.4 g 6-nitroanthranilic acid (0.6 mol) and 98.5 g 6,6-dimethylfulvene (1.5 equivalents) in 700 ml dimethoxyethane was added dropwise to a solution of 96.3 g t-butylnitrite (1.4 equivalents) in 2 litres 1,2-dimethoxyethane at 72° C. under nitrogen atmosphere. Gas-formation started and the temperatur rose to 79° C. The gas-formation stopped after 30 minutes. The reaction mixture was stirred for 3 hours and then cooled to ambient temperature. The reaction mixture was evaporated and purified on silica gel in hexane-ethyl acetate (95:5) to give 76.7 g of the desired product as yellow crystals (m.p. 94-95° C.). $^1$H-NMR (CDCl$_3$), ppm: 7.70 (d, 1H), 7.43 (d, 1H), 7.06 (t, 1H), 6.99 (m, 2H), 5.34 (brd s, 1H), 4.47 (brd s, 1H), 1.57 (2 d, 6H). $^{13}$C-NMR (CDCl$_3$), ppm: 159.83, 154.30, 147.33, 144.12, 142.89, 141.93, 125.23 (2×), 119.32, 105.68, 50.51, 50.44, 19.05, 18.90.

EXAMPLE 10

This Example illustrates the preparation of 9-isopropylidene-5-nitro-benzonorbornene (Compound No. 34.02)

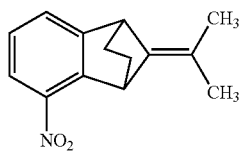

49.0 g 9-isopropylidene-5-nitro-benzonorbornadiene (Compound No. 32.02) were dissolved in 500 ml tetrahydrofuran and hydrogenated at 20° C. in the presence of 5 g Rh(PPh$_3$)$_3$Cl (Wilkinson's catalyst). The reaction ceased after the uptake of 1 equivalent of hydrogen (after 2.5 hours). Evaporation and filtration of the crude product on silica gel in ethyl acetate-hexane-(1:6), followed by trituration in hexane gave 48.3 g of the desired product as a solid (yield: 98%; m.p. 88-89° C.).

FORMULATION EXAMPLES FOR COMPOUNDS OF FORMULA (I)

Example F-1.1 to F-1.3

Emulsifiable Concentrates

| Components | F-1.1 | F-1.2 | F-1.3 |
|---|---|---|---|
| compound of Tables 1 to 30 | 25% | 40% | 50% |
| calcium dodecylbenzenesulfonate | 5% | 8% | 6% |
| castor oil polyethylene glycol ether (36 mol ethylenoxy units) | 5% | — | — |
| tributylphenolpolyethylene glycol ether (30 mol ethylenoxy units) | — | 12% | 4% |
| cyclohexanone | — | 15% | 20% |
| xylene mixture | 65% | 25% | 20% |

Emulsions of any desired concentration can be prepared by diluting such concentrates with water.

Example F-2

Emulsifiable Concentrate

| Components | F-2 |
|---|---|
| compound of Tables 1 to 30 | 10% |
| octylphenolpolyethylene glycol ether (4 to 5 mol ethylenoxy units) | 3% |
| calcium dodecylbenzenesulfonate | 3% |
| castor oil polyglycol ether (36 mol ethylenoxy units) | 4% |
| cyclohexanone | 30% |
| xylene mixture | 50% |

Emulsions of any desired concentration can be prepared by diluting such concentrates with water.

Examples F-3.1 to F-3.4

Solutions

| Components | F-3.1 | F-3.2 | F-3.3 | F-3.4 |
|---|---|---|---|---|
| compound of Tables 1 to 30 | 80% | 10% | 5% | 95% |
| propylene glycol monomethyl ether | 20% | — | — | — |
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| benzin (boiling range: 160-190°) | — | — | 94% | — |

The solutions are suitable for use in the form of microdrops.

Examples F-4.1 to F-4.4

Granulates

| Components | F-4.1 | F-4.2 | F-4.3 | F-4.4 |
|---|---|---|---|---|
| compound of Tables 1 to 30 | 5% | 10% | 8% | 21% |
| kaolin | 94% | — | 79% | 54% |
| highly dispersed silicic acid | 1% | — | 13% | 7% |
| attapulgite | — | 90% | — | 18% |

The novel compound is dissolved in dichloromethane, the solution is sprayed onto the carrier and the solvent is then removed by distillation under vacuum.

Examples F-5.1 and F-5.2

Dusts

| Components | F-5.1 | F-5.2 |
|---|---|---|
| compound of Tables 1 to 30 | 2% | 5% |
| highly dispersed silicic acid | 1% | 5% |
| talcum | 97% | — |
| kaolin | — | 90% |

Ready for use dusts are obtained by intimately mixing all components.

Examples F-6.1 to F-6.3

Wettable Powders

| Components | F-6.1 | F-6.2 | F-6.3 |
|---|---|---|---|
| compound of Tables 1 to 30 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7 to 8 mol ethylenoxy units) | — | 2% | — |
| highly dispersed silicic acid | 5% | 10% | 10% |
| kaolin | 62% | 27% | — |

All components are mixed and the mixture is thoroughly ground in a suitable mill to give wettable powders which can be diluted with water to suspensions of any desired concentration.

Example F7

Flowable Concentrate for Seed Treatment

| | |
|---|---|
| compound of Tables 1 to 30 | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

BIOLOGICAL EXAMPLES

Fungicidal Actions

Example B-1

Action Against *Puccinia recondita*/Wheat (Brownrust on Wheat)

1 week old wheat plants cv. Arina are treated with the formulated test compound (0.02% active ingredient) in a spray chamber. One day after application, the wheat plants are inoculated by spraying a spore suspension ($1 \times 10^5$ uredospores/ml) on the test plants. After an incubation period of 2 days at 20° C. and 95% r.h. the plants are kept in a greenhouse for 8 days at 20° C. and 60% r.h. The disease incidence is assessed 10 days after inoculation.

Compounds 1.01, 1.11, 1.21, 12.01, 12.11, 12.21, 13.01, 13.11, 13.21, 20.01, 20.11, 20.21, 27.01, 27.11 and 27.21 show good activity in this test (<20% infestation).

Example B-2

Action Against *Podosphaera leucotricha*/Apple (Powdery Mildew on Apple)

5 week old apple seedlings cv. McIntosh are treated with the formulated test compound (0.02% active ingredient) in a spray chamber. One day after, the application apple plants are inoculated by shaking plants infected with apple powdery mildew above the test plants. After an incubation period of 12 days at 22° C. and 60% r.h. under a light regime of $^{14}/_{10}$ hours (light/dark) the disease incidence is assessed.

Compounds 1.01, 1.11, 1.21, 12.01, 12.11, 12.21, 13.01, 13.11, 13.21, 20.01, 20.11, 20.21, 27.01, 27.11 and 27.21 each exhibit strong efficacy (<20% infestation).

Example B-3

Action Against *Venturia inaequalis*/Apple (Scab on Apple)

4 week old apple seedlings cv. McIntosh are treated with the formulated test compound (0.02% active ingredient) in a spray chamber. One day after application, the apple plants are inoculated by spraying a spore suspension ($4 \times 10^5$ conidia/ml) on the test plants. After an incubation period of 4 days at 21° C. and 95% r.h. the plants are placed for 4 days at 21° C. and 60% r.h. in a greenhouse. After another 4 day incubation period at 21° C. and 95% r.h. the disease incidence is assessed.

Compounds 1.01, 1.11, 1.21, 12.01, 12.11, 12.21, 13.01, 13.11, 13.21, 20.01, 20.11, 20.21, 27.01, 27.11 and 27.21 each exhibit strong efficacy (<20% infestation).

Example B-4

Action Against *Erysiphe graminis*/Barley (Powdery Mildew on Barley)

1 week old barley plants cv. Regina are treated with the formulated test compound (0.02% active ingredient) in a spray chamber. One day after application, the barley plants are inoculated by shaking powdery mildew infected plants above the test plants. After an incubation period of 6 days at 20° C./18° C. (day/night) and 60% r.h. in a greenhouse the disease incidence is assessed.

Compounds 1.01, 1.11, 1.21, 12.01, 12.11, 12.21, 13.01, 13.11, 13.21, 20.01, 20.11, 20.21, 27.01, 27.11 and 27.21 each exhibit strong efficacy (<20% infestation).

Example B-5

Action Against *Botrytis cinerea*/Grape (*Botrytis* on Grapes)

5 week old grape seedlings cv. Gutedel are treated with the formulated test compound (0.02% active ingredient) in a spray chamber. Two days after application, the grape plants are inoculated by spraying a spore suspension ($1 \times 10^6$ conidia/ml) on the test plants. After an incubation period of 4 days at 21° C. and 95% r.h. in a greenhouse the disease incidence is assessed.

Compounds 1.01, 1.11, 1.21, 12.01, 12.11, 12.21, 13.01, 13.11, 13.21, 20.01, 20.11, 20.21, 27.01, 27.11 and 27.21 each show good activity in this test (<50% disease incidence).

Example B-6

Action Against *Botrytis cinerea*/Tomato (*Botrytis* on Tomatoes)

4 week old tomato plants cv. Roter Gnom are treated with the formulated test compound (0.02% active ingredient) in a spray chamber. Two days after application, the tomato plants are inoculated by spraying a spore suspension ($1 \times 10^5$ conidia/ml) on the test plants. After an incubation period of 4 days at 20° C. and 95% r.h. in a growth chamber the disease incidence is assessed.

Compounds 1.01, 1.11, 1.21, 12.01, 12.11, 12.21, 13.01, 13.11, 13.21, 20.01, 20.11, 20.21, 27.01, 27.11 and 27.21 each exhibit good efficacy (<50% disease incidence).

Example B-7

Action Against *Septoria nodorum*/Wheat (*Septoria* Leaf Spot on Wheat)

1 week old wheat plants cv. Arina are treated with the formulated test compound (0.02% active ingredient) in a spray chamber. One day after application, the wheat plants are inoculated by spraying a spore suspension ($5 \times 10^5$ conidia/ml) on the test plants. After an incubation period of 1 day at 20° C. and 95% r.h. the plants are kept for 10 days at 20° C. and 60% r.h. in a greenhouse. The disease incidence is assessed 11 days after inoculation.

Compounds 1.01, 1.11, 1.21, 12.01, 12.11, 12.21, 13.01, 13.11, 13.21, 20.01, 20.11, 20.21, 27.01, 27.11 and 27.21 each show good activity in this test (<50% disease incidence).

Example B-8

Action Against *Helminthosporium teres*/Barley (Net Blotch on Barley)

1 week old barley plants cv. Regina are treated with the formulated test compound (0.02% active ingredient) in a spray chamber. Two days after application, the barley plants are inoculated by spraying a spore suspension ($3 \times 10^4$ conidia/ml) on the test plants. After an incubation period of 4 days at 20° C. and 95% r.h. in a greenhouse the disease incidence is assessed.

Compounds 1.01, 1.11, 1.21, 12.01, 12.11, 12.21, 13.01, 13.11, 13.21, 20.01, 20.11, 20.21, 27.01, 27.11 and 27.21 each show good activity in this test (<20% disease incidence).

Example B-9

Action Against *Alternaria solani*/Tomato (Early Blight on Tomatoes)

4 week old tomato plants cv. Roter Gnom are treated with the formulated test compound (0.02% active ingredient) in a spray chamber. Two days after application, the tomato plants are inoculated by spraying a spore suspension ($2 \times 10^5$ conidia/ml) on the test plants. After an incubation period of 3 days at 20° C. and 95% r.h. in a growth chamber the disease incidence is assessed.

Compounds 1.01, 1.11, 1.21, 12.01, 12.11, 12.21, 13.01, 13.11, 13.21, 20.01, 20.11, 20.21, 27.01, 27.11 and 27.21 each show good activity in this test (<20% disease incidence).

Example B-10

Action Against *Uncinula necator*/Grape (Powdery Mildew on Grapes)

5 week old grape seedlings cv. Gutedel are treated with the formulated test compound (0.02% active ingredient) in a spray chamber. One day after application, the grape plants are inoculated by shaking plants infected with grape powdery mildew above the test plants. After an incubation period of 7 days at 26° C. and 60% r.h. under a light regime of 14/10 hours (light/dark) the disease incidence is assessed.

Compounds 1.01, 1.11, 1.21, 12.01, 12.11, 12.21, 13.01, 13.11, 13.21, 20.01, 20.11, 20.21, 27.01, 27.11 and 27.21 each show good activity in this test (<20% disease incidence).

Example B-11

Systemic Action Against *Erysiphe graminis*/Barley (Powdery Mildew on Barley) (Pouch Test)

The formulated test compound (0.002% active ingredient) is applied into a pouch which is previously equipped with a filter paper. After the application barley seeds (cv. Express) are sown into the upper fault of the filter paper. The prepared pouches are then incubated at 23° C./18° C. (day/night) and 80% r.h. One week after sowing barley plants are inoculated by shaking powdery mildew infected plants above the test plants. After an incubation period of 6 days the disease incidence is assessed. The efficacy of each test compound is used as an indicator for systemic activity.

Compounds 1.01, 1.11, 1.21, 12.01, 12.11, 12.21, 13.01, 13.11, 13.21, 20.01, 20.11, 20.21, 27.01, 27.11 and 27.21 each show good activity in this test (<50% disease incidence).

Example B-12

Action Against *Fusarium culmorum*/Wheat
(*Fusarium* Head Blight on Wheat) (Pouch Test)

A conidia suspension of *F. culmorum* ($7 \times 10^5$ conidia/ml) is mixed with the formulated test compound (0.002% active ingredient). The mixture is applied into a pouch which is previously equipped with a filter paper. After the application wheat seeds (cv. Orestis) are sown into the upper fault of the filter paper. The prepared pouches are then incubated for 11 days at ca. 10-18° C. and 100% r.h. with a daily light period of 14 hours. The evaluation is made by assessing the degree of disease occurrence in the form of brown lesions on the roots.

Compounds 1.01, 1.11, 1.21, 12.01, 12.11, 12.21, 13.01, 13.11, 13.21, 20.01, 20.11, 20.21, 27.01, 27.11 and 27.21 each show good activity in this test (<50% disease incidence).

Example B-13

Action Against *Gaeumannomyces graminis*/Wheat
(Take-all on Wheat) (Pouch Test)

A defined amount of mycelium of *G. graminis* is mixed with water. The formulated test compound (0.002% active ingredient) is added to the mycelium suspension. The mixture is applied into a pouch which is previously equipped with a filter paper. After the application wheat seeds (cv. Orestis) are sown into the upper fault of the filter paper. The prepared pouches are then incubated for 14 days at 18° C./16° C. (day/night) and 80% r.h. with a daily light period of 14 hours. The evaluation is made by assessing the degree of root browning.

Compounds 1.01, 1.11, 1.21, 12.01, 12.11, 12.21, 13.01, 13.11, 13.21, 20.01, 20.11, 20.21, 27.01, 27.11 and 27.21 each show good activity in this test (<50% disease incidence).

Example B-14

Action Against *Puccinia recondita*/Wheat
(Brownrust on Wheat) (Pouch Test)

Formulated test compound (0.002% active ingredient) is applied into a pouch which is previously equipped with a filter paper. After the application wheat seeds (cv. Arina) are sown into the upper fault of the filter paper. The prepared pouches are then incubated at 23° C./18° C. (day/night) and 80% r.h. One week after sowing, the wheat plants are inoculated by spraying a spore suspension ($1 \times 10^5$ uredospores/ml) on the test plants. After an incubation period of 1 day at 23° C. and 95% r.h. the plants are kept for 9 days at 20° C./18° C. (day/night) and 80% r.h. The disease incidence is assessed 10 days after inoculation. The efficacy of each test compound is used as an indicator for systemic activity.

Compounds 1.01, 1.11, 1.21, 12.01, 12.11, 12.21, 13.01, 13.11, 13.21, 20.01, 20.11, 20.21, 27.01, 27.11 and 27.21 each show good activity in this test (<50% disease incidence).

Example B-15

Action Against *Rhizoctonia solani*/Rice (Sheath
Blight on Rice) (Pouch Test)

A defined amount of mycelium of *R. solani* is mixed with water. The formulated test compound (0.002% active ingredient) is added to the mycelium suspension. The mixture is applied into a pouch which is previously equipped with a filter paper. After the application rice seeds (cv. Koshihikari) are sown into the upper fault of the filter paper. The prepared pouches are then incubated for 10 days at 23° C./21° C. (day/night) and 100% r.h. with a daily light period of 14 hours. The evaluation is made by assessing the degree of disease occurrence in the form of brown lesions on the roots.

Compounds 1.01, 1.11, 1.21, 12.01, 12.11, 12.21, 13.01, 13.11, 13.21, 20.01, 20.11, 20.21, 27.01, 27.11 and 27.21 each show good activity in this test (<50% disease incidence).

Example B-16

Action Against *Septoria nodorum*/Wheat (*Septoria*
Leaf Spot on Wheat) (Pouch Test)

The formulated test compound (0.002% active ingredient) is applied into a pouch which is previously equipped with a filter paper. After the application, wheat seeds (cv. Arina) are sown into the upper fault of the filter paper. The prepared pouches are then incubated at 23° C./18° C. (day/night) and 80% r.h. One week after sowing, the wheat plants are inoculated by spraying a spore suspension ($5 \times 10^5$ conidia/ml) on the test plants. After an incubation period of 1 day at 23° C. and 95% r.h. the plants are kept for 9 days at 20° C./18° C. (day/night) and 80% r.h. The disease incidence is assessed 8 days after inoculation. The efficacy of each test compound is used as an indicator for systemic activity.

Compounds 1.01, 1.11, 1.21, 12.01, 12.11, 12.21, 13.01, 13.11, 13.21, 20.01, 20.11, 20.21, 27.01, 27.11 and 27.21 each show good activity in this test (<50% disease incidence).

Example B-17

Action Against *Septoria tritici*/Wheat (*Septoria* Leaf
Spot on Wheat)

2 week old wheat plants cv. Riband are treated with the formulated test compound (0.02% active ingredient) in a spray chamber. One day after application, wheat plants are inoculated by spraying a spore suspension ($10 \times 10^5$ conidia/ml) on the test plants. After an incubation period of 1 day at 23° C. and 95% r.h., the plants are kept for 16 days at 23° C. and 60% r.h. in a greenhouse. The disease incidence is assessed 18 days after inoculation.

Compounds 1.01, 1.11, 1.21, 12.01, 12.11, 12.21, 13.01, 13.11, 13.21, 20.01, 20.11, 20.21, 27.01, 27.11 and 27.21 each show good activity in this test (<20% disease incidence).

The invention claimed is:
1. A compound of the formula (D):

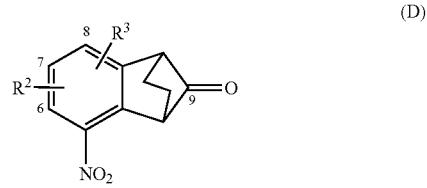

where $R^2$ and $R^3$ are each, independently, hydrogen, halo, $C_{1-4}$ alkyl, $C_{1-4}$ alkoxy, $C_{1-4}$ haloalkyl or $C_{1-4}$ haloalkoxy.

2. A compound of claim 1, wherein $R^2$ and $R^3$ are each, independently, hydrogen, fluoro, chloro or bromo, methyl or methoxy.

3. A compound of claim 1, wherein (i) one of $R^2$ and $R^3$ is hydrogen and (ii) one of $R^2$ and $R^3$ is fluoro, chloro, bromo or methyl.

4. A compound of claim 1, wherein $R^2$ and $R^3$ are both hydrogen, both fluoro, both chloro both bromo, or both methoxy.

5. A compound of claim 4, wherein $R^2$ and $R^3$ are both hydrogen.

6. A compound of claim 1, wherein $R^2$ is hydrogen, 6-halo, 7-halo or 7-$C_{1-4}$ alkyl, and $R^3$ is hydrogen.

7. A compound of claim 6, wherein $R^2$ is 6-bromo, 7-chloro, 7-fluoro or 7-methyl, and $R^3$ is hydrogen.

8. A compound of claim 1, wherein $R^2$ and $R^3$ together are 6,8-di-$C_{1-4}$ alkoxy, 6,8-dihalo or 7,8-di-$C_{1-4}$ alkoxy.

9. A compound of claim 8, wherein $R^2$ and $R^3$ together are 6,8-dimethoxy, 6,8-dibromo or 7,8-dimethoxy.

* * * * *